(12) United States Patent
Walther

(10) Patent No.: US 12,290,697 B2
(45) Date of Patent: May 6, 2025

(54) PROCESS CONTROL FOR ATMOSPHERIC PLASMA TREATMENT OF SURFACES

(71) Applicant: Steven R. Walther, Andover, MA (US)

(72) Inventor: Steven R. Walther, Andover, MA (US)

( * ) Notice: Subject to any disclaimer, the term of this patent is extended or adjusted under 35 U.S.C. 154(b) by 1040 days.

(21) Appl. No.: 17/246,653

(22) Filed: May 2, 2021

(65) Prior Publication Data
US 2021/0339034 A1 Nov. 4, 2021

Related U.S. Application Data

(60) Provisional application No. 63/019,609, filed on May 4, 2020.

(51) Int. Cl.
| | | |
|---|---|---|
| *A61B 18/00* | (2006.01) | |
| *A61B 18/04* | (2006.01) | |
| *A61B 18/12* | (2006.01) | |
| *A61B 18/18* | (2006.01) | |
| *A61L 2/00* | (2006.01) | |
| *A61L 2/24* | (2006.01) | |
| *A61N 1/40* | (2006.01) | |
| *A61N 1/44* | (2006.01) | |
| *H05H 1/00* | (2006.01) | |

(Continued)

(52) U.S. Cl.
CPC .............. *A61N 1/44* (2013.01); *A61B 18/042* (2013.01); *A61B 18/1815* (2013.01); *A61L 2/0011* (2013.01); *A61L 2/24* (2013.01); *A61N 1/403* (2013.01); *H05H 1/0037* (2013.01); *H05H 1/0043* (2013.01); *H05H 1/2406* (2013.01); *H05H 1/461* (2021.05); *H05H 1/4645* (2021.05); *A61L 2202/11* (2013.01); *A61L 2202/14* (2013.01)

(58) Field of Classification Search
CPC ........ A61N 1/44; A61N 1/403; H05H 1/4645; H05H 1/461; H05H 1/0037; H05H 1/0043; H05H 1/2406; H05H 1/00–48; A61B 18/042; A61B 18/1815; A61B 2018/122; A61B 2018/1226; A61L 2/0011; A61L 2/24; A61L 2202/11; A61L 2202/14

See application file for complete search history.

(56) References Cited

U.S. PATENT DOCUMENTS

| | | | | |
|---|---|---|---|---|
| 2016/0138006 A1* | 5/2016 | Canady | ................ | A61B 18/042 606/34 |
| 2016/0329193 A1* | 11/2016 | Sieber | ...................... | H05H 1/46 |

(Continued)

OTHER PUBLICATIONS

Hak Jun Ahn et al., "Targeting Cancer Cells with Reactive Oxygen and Nitrogen Species Generated by Atmospheric-Pressure Air Plasma", Jan. 2014 (Year: 2014).*

(Continued)

*Primary Examiner* — Adam Z Minchella
(74) *Attorney, Agent, or Firm* — Robert Kaim

(57) ABSTRACT

Disclosed is a system and method for delivering reactive species from a plasma to a treatment area by scanning a linear array of stacked plasma elements across the treatment area. Reactive species output from each plasma element is calibrated, and during scanning each plasma element is modulated with a uniformity modulation and a dose modulation, enabling a predetermined contour dose distribution of reactive species to be delivered to the treatment area.

23 Claims, 17 Drawing Sheets

(51) Int. Cl.
  *H05H 1/24*    (2006.01)
  *H05H 1/46*    (2006.01)

(56) References Cited

U.S. PATENT DOCUMENTS

2017/0094769 A1* 3/2017 Eckert .................. A61B 18/042
2020/0069355 A1* 3/2020 Keidar .................. A61N 2/002

OTHER PUBLICATIONS

Brany, Dusan et al., "Cold Atmospheric Plasma: A Powerful Tool for Modern Medicine", Apr. 22, 2020 (Year: 2020).*
Kaushik, Neha et al., "Responses of Solid Tumor Cells in DMEM to Reactive Oxygen Species Generated by Non-Thermal Plasma and Chemically Induced ROS Systems", Feb. 26, 2015 (Year: 2015).*
Klaus Dieter Weltmann "Atmospheric-pressure plasma sources: Prospective tools for plasma medicine", Apr. 20, 2010, Pure Appl. Chem., vol. 82, No. 6, pp. 1223-1237.

\* cited by examiner

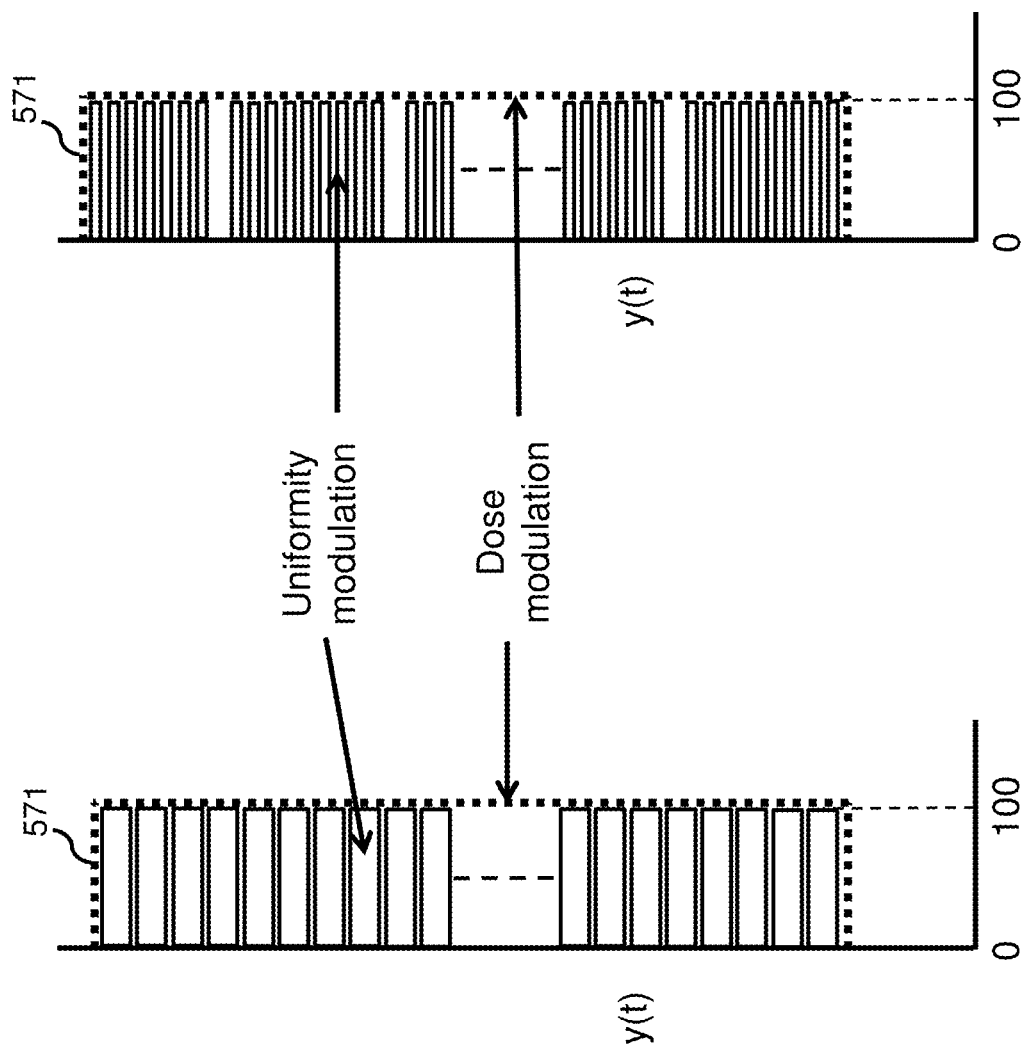

PROCESS CONTROL FOR ATMOSPHERIC PLASMA TREATMENT OF SURFACES

CROSS-REFERENCE TO RELATED APPLICATIONS

This application claims the benefit and priority of U.S. Provisional patent application Ser. No. 63/019,609 filed May 4, 2020 entitled PROCESS CONTROL FOR ATMOSPHERIC PLASMA TREATMENT OF SURFACES, the entire disclosure of which is incorporated herein by reference.

FIELD OF THE INVENTION

Example embodiments of the present disclosure relate to the field of surface treatment with atmospheric plasma. In particular, the disclosure relates to a method and apparatus for process control by which treatment of a defined area on a surface can be made uniform and repeatable.

BACKGROUND OF THE INVENTION

Low temperature atmospheric plasma or cold atmospheric plasma (CAP) has been applied to surfaces to achieve biological effects such as wound treatment, sterilization, cancer cell inactivation, and others. The plasma is used to create reactive species, such as reactive oxygen or nitrogen species. This may be either direct (for example, reactive gaseous plasma species interacting directly with cells) or indirect (for example, where reactive plasma species interact with a liquid interface to the surface and create liquid phase reactive species).

Atmospheric plasmas are known in the art and can be established through many different means. See, for example, Weltmann et. al., Pure Appl. Chem., Vol. 82, No. 6, pp. 1223-1237, April 2010, "Atmospheric-pressure plasma sources: Prospective tools for plasma medicine". Most common atmospheric plasma sources are dielectric barrier discharges (DBD), which use AC voltages or voltage pulses to create the plasma. Other common atmospheric discharges use microwave or radio frequency (RF) power to sustain the plasma. The 'low temperature' aspect refers to the temperature of the neutral gas in the plasma maintaining a temperature close to room temperature.

The gases supplied to the plasma typically comprise a carrier gas and a mixture of one or more precursor gases that are precursors to reactive species, such as oxygen and nitrogen. The precursor gases are hereinafter referred to as "reactive gas". Examples of reactive species include radicals, such as $O^*$ or $N_xO_y^*$. The carrier gas may typically be helium, argon or nitrogen. The carrier gas plays an active role in creation of reactive species from the reactive gas, through energetic long-lived metastable species or ions created by interaction with ions from the carrier gas.

Current state of the art for applying CAP is the use of a single small plasma source that is manually moved over the treatment area for a fixed amount of time while using a defined level of plasma power. Unfortunately, this has no mechanism to measure what is produced by the plasma or to confirm that the treatment is uniform over the desired treatment area. There is no 'process control' in the formal sense of a feedback-controlled monitored process, and hence there is no realistic expectation that treatment effects are repeatable and uniform.

Keidar (US Patent Application 2020/0069355) has disclosed use of a 'cold atmospheric plasma jet' to treat cancerous cells, together with a sensor to detect 'cell viability'. However, Keidar's sensor is directed to measuring a characteristic of the treatment surface, and there is no attempt to measure or control uniformity of output from the plasma jet.

Therefore, it is desirable to have a source capable of uniform plasma output, and to introduce a form of process control that incorporates measurement of reactive species output together with feedback control to achieve more uniform and repeatable results.

SUMMARY OF THE INVENTION

In one aspect, disclosed herein is a system and method for delivering a predetermined dose distribution of a reactive species output from a plasma array to a treatment area. The plasma array comprises a linear array of at least two plasma elements stacked linearly along an array axis, wherein each plasma element is an atmospheric plasma source and wherein each plasma element has an on state producing the reactive species output and an off state wherein the reactive species output is zero. The reactive species output is calibrated by measuring a reactive species concentration for each one of the plasma elements and deriving an element scaling factor for each one of the plasma elements, wherein each element scaling factor is inversely proportional to the corresponding reactive species concentration.

The plasma array is scanned across the treatment area with one or more scans in a back-and-forth scan direction perpendicular to the array axis and each plasma element is controlled during the scanning with a uniformity modulation and a dose modulation. The uniformity modulation controls the reactive species output of each plasma element to be proportional to the corresponding element scaling factor, and the dose modulation controls the on state and the off state of each plasma element to deliver the predetermined dose distribution.

In another aspect, a system is disclosed for delivering reactive species from a plasma array to a treatment area, and for performing an in-situ calibration of the reactive species. The plasma array comprises a linear array of at least two plasma elements stacked linearly along an array axis, wherein each plasma element is an atmospheric plasma source. The system comprises an array scanning system configured to scan the plasma array across the treatment area with one or more scans in a back-and-forth scan direction perpendicular to the array axis, and a point probe having a probe surface comprising a material which is reactive with the reactive species. A probe translation system is configured to translate the probe in a direction parallel to the array axis to a plurality of probe measurement positions. During operation, reactive species output from the plasma array is coupled to the treatment area and to the point probe, and the point probe measures a reaction rate of the reactive species output with the probe surface during at least one scan at each of the probe measurement positions.

BRIEF DESCRIPTION OF THE DRAWINGS

FIG. 5E illustrates a combined uniformity modulation and dose modulation of a single plasma element.

FIG. 5F illustrates an alternative combined uniformity modulation and dose modulation of a single plasma element.

DETAILED DESCRIPTION OF PREFERRED EMBODIMENT

Figure 1A:
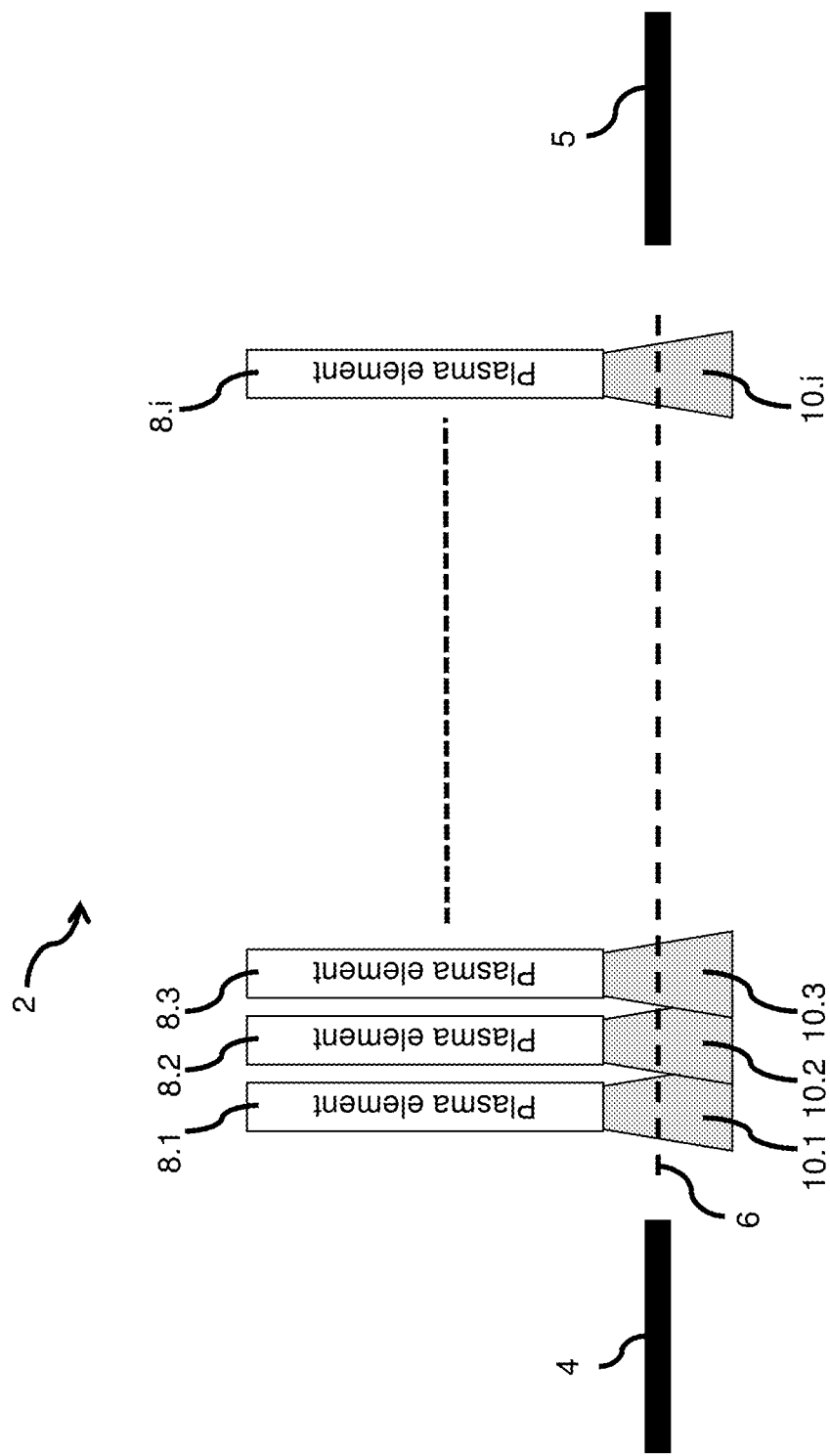
FIG. 1A is a schematic representation of a plasma array and longitudinal detection system operating in an atmospheric environment in accordance with the present disclosure.

The invention uses an array of individual plasma sources, hereinafter referred to as a "plasma array". Each individual source is hereinafter referred to as a "plasma element". In an embodiment, the invention utilizes a one-dimensional (1D) plasma array to create a line of plasma output which may then be mechanically scanned across a desired treatment area.

Reactive species in the plasma output are measured, either directly (direct measurement of reactive species concentration) or indirectly (measurement correlated to reactive species concentration) to provide a feedback signal for both uniformity of output and for the dose rate (flux rate of reactive species, measured in number/cm/sec) at a defined distance downstream from the plasma source. The feedback signal allows the plasma elements to be controlled so as to deliver a uniform dose rate or a predetermined non-uniform dose rate, and to determine the treatment time required to deliver a desired total dose to a treatment area.

Methods of direct measurement of the reactive species output include Fourier Transform Infrared (FTIR) absorption and Optical Emission Spectroscopy (OES), both of which can be used to directly measure reactive species concentration. Methods of indirect measurement of the reactive species output include electrical probes (for example, Langmuir probes), thermal probes, reaction probes (oxidation sensors) and others. Other methods of direct and indirect measurement of the reactive species output may be devised, and all are within the scope of the present disclosure.

The measurement signal may represent reactive species output at a sample point, or integrated over a line path. To determine output magnitude for each plasma element requires either multiple point sensors, or a moveable point sensor, or a line path sensor. The output magnitude of each plasma element may be determined by multiple measurements with selective activation of individual plasma elements. For example, consecutive measurements may be made with each plasma element individually activated. Alternatively, consecutive measurements may be made with incremental activation of plasma elements, wherein, respectively, one, two, three . . . all plasma elements are sequentially activated. In the latter case, the incremental sensor signals may be correlated with the output of each additionally activated plasma element. In yet another alternative, consecutive measurements may be made with incremental deactivation of plasma elements, starting with all plasma elements activated and sequentially deactivating each of the plasma elements. In this case, reduction of sensor signals may be correlated with the output of each additionally inactivated plasma element. Knowledge of the magnitude of reactive species output from each plasma element then enables uniformity across the plasma array to be achieved by controlling the output of each element.

Control of reactive species output from each plasma element (hereinafter referred to as "modulation") can be achieved through several means. In an embodiment which is especially useful for DBD plasma elements, each plasma element may be rapidly turned 'on' or 'off' electrically so that average output can be controlled by the average amount of 'on' time. Fast on/off switching may be achieved using a fast electrical switch, or by rapidly controlling on/off pulsing of a pulse power supply or master oscillator. For other types of plasma elements, such as microwave or RF plasma, rapid electrical switching may not be practical because of difficulty re-igniting the plasma, and in such cases rapid control of the reactive gas flow may be used for modulation. Rapid control of reactive gas flow may be used for any plasma type. Other mechanisms are possible, including power modulation (instantaneous power to plasma) or physical shutters.

Modulation by rapid control of gas flow may be implemented through the use of a continuous carrier gas flow (to maintain the plasma), while rapidly modulating the flow of the reactive gas. Thus the average flow of reactive gas becomes the output control mechanism for each plasma element. One example of fast flow modulation would be the use of a fast valve (for example, a piezoelectric valve) in series with a known conductance to supply reactive gas to each plasma element.

"On/off" control of either power supplies or gas flow is a preferred modulation method because the average output is directly proportional to the "on" time. Other modulation methods are possible, but linearity may be uncertain and may need to be verified. For example, a 10% increase of reactive gas flow, or a 10% increase of plasma power, may not result in a 10% increase of reactive species in the plasma. The invention of the present disclosure incorporates empirical calibration methods to account for any non-linearities by independently calibrating the quantity of reactive species in the plasma. A calibration is only valid for a particular set of plasma parameters, such as total gas flow and plasma power. A further advantage of modulation by rapid "on/off" switching is that during "on" times all plasma parameters maybe unchanged from those used during calibration.

At a system level, the feedback and control mechanisms provide a uniform reactive species output across the length of the plasma array. Alternatively, the output may be configured to provide a pre-configured non-uniform distribution. Furthermore, the dose rate of reactive species is calibrated and known, and may then be used to treat a treatment surface having a pre-configured treatment area and dose distribution within the treatment area. Such knowledge of the treatment area and dose distribution may then be used to define how the plasma array is moved to distribute the dose of reactive species within the treatment area. The plasma array may be mechanically scanned over the treatment surface (for example, 1D motion orthogonal to the array axis) and the dose per pass calculated based on the dose rate and the scan velocity. In one embodiment, the system may account for a non-standard distance to the surface using an empirical lookup table that correlates effective dose rate versus distance. In an alternative embodiment, a plasma applicator comprising the plasma array and a mechanical scanning system may be used to maintain a known distance to the surface during scanning, and in some embodiments this distance may be constant. In yet another embodiment the plasma applicator may comprise one or more position sensors to measure the position, orientation and velocity of the plasma array relative to the treatment surface.

A desired treatment area is likely to be non-rectangular, hence the plasma elements may be controlled during scanning to deliver any desired shape to the dose pattern on the treatment surface. This may be achieved in the same fashion as uniformity is achieved, by individually modulating each array element, preferably by controlling reactive output to be "on" or "off" as needed to achieve the desired dose pattern. Hereinafter, modulation of plasma elements to achieve uniformity of reactive species output along the array axis is referred to as "uniformity modulation", and modulation of plasma elements to deliver any desired shape to the dose pattern on the treatment surface is referred to as "dose modulation".

It may also be desired that the treatment supply varying dose within the treatment area (for example, a contour dose map). This may be achieved within the same control system by shifting the "on/off" locations for each plasma array element on each pass over the treatment area during scanning. In the embodiment wherein the plasma applicator comprises one or more position sensors, manual (handheld) scanning of the plasma array may be employed with a degree of uniformity and repeatability similar to that achieved with a mechanical scanning system.

FIG. 1A is a schematic representation of a 1D plasma array 2 operating in an atmospheric environment. Plasma array 2 comprises plasma elements 8.1, 8.2, 8.3 . . . 8.$i$ wherein i is the total number of plasma elements in the plasma array. Plasma elements 8.1, 8.2, 8.3 . . . 8.$i$ are stacked linearly along an array axis 6. Each plasma element 8.1, 8.2, 8.3 . . . 8.$i$ emits a plasma output 10.1, 10.2, 10.3 . . . 10.$i$ respectively, wherein each plasma output comprises reactive species and carrier gas species. Each one of plasma output 10.1, 10.2, 10.3 . . . 10.$i$ is individually controllable and the output of reactive species from each plasma element can be measured to determine the spatial distribution and magnitude of each reactive species output. Measurement of reactive species is made by detectors 4 and 5 aligned parallel to array axis 6. Note that detectors 4 and 5 may be detector emitters and/or detector receivers. The detection system of FIG. 1A is a longitudinal detection system in that detectors 4 and 5 are measuring parallel to array axis 6. In a preferred embodiment, the longitudinal detection system is used for FTIR detection of the reactive species, in which case detector 4 may be an infrared emitter and detector 5 may be an infrared receiver. In alternative embodiments, detectors 4 and 5 may be optical receivers for OES measurements. Alternatively, detector 4 may be an optical emitter/receiver and detector 5 an optical mirror reflecting light back to detector 4. Note that detectors 4 and 5 may make measurements of reactive species without actually contacting the plasma.

Figure 1B:
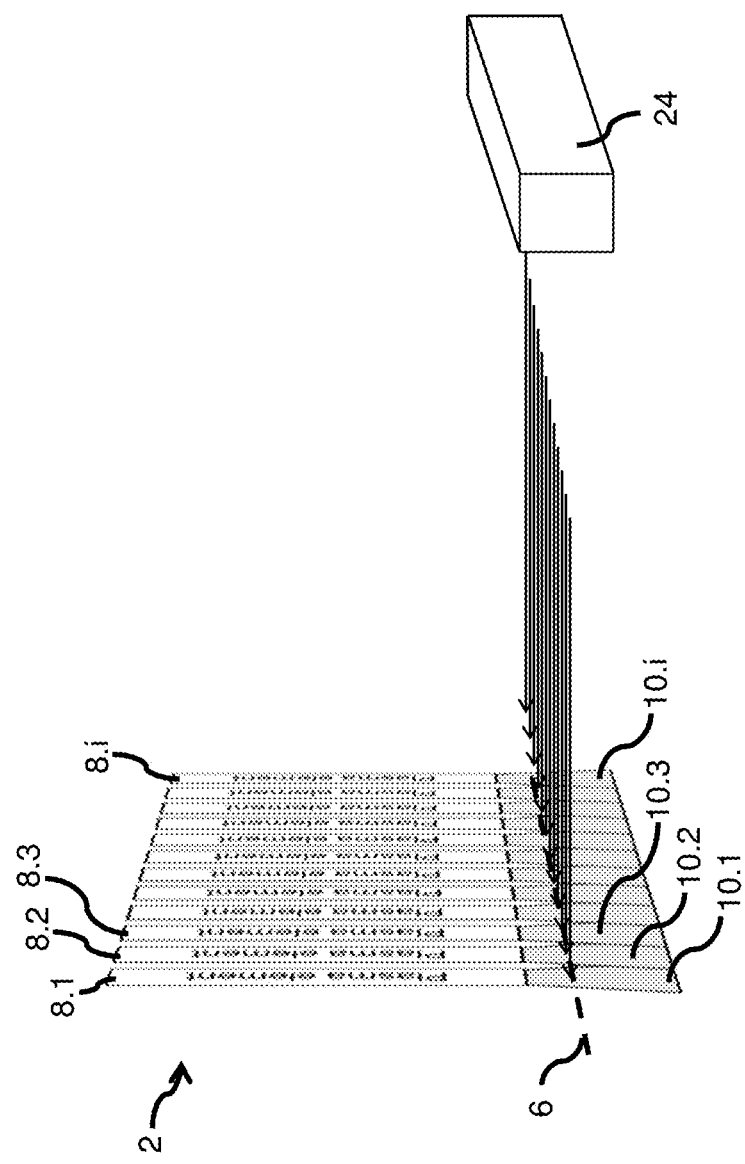
FIG. 1B is a schematic representation of a plasma array and transverse detection system operating in an atmospheric environment in accordance with the present disclosure.

FIG. 1B is a schematic representation of plasma array 2 and a transverse detection system 24. In this implementation detection system 24 measures transverse to array axis 6 to determine the spatial distribution and magnitude of the reactive species output. In a preferred embodiment, detection system 24 may comprise a linear array of individual detectors arranged in a line parallel to array axis 6. In another preferred embodiment, there is a one-to-one correspondence between each plasma element 8.1, 8.2, 8.3 . . . 8.$i$ and each one of the individual detectors of detection system 24, such that detection system 24 comprises a total of i individual detectors. In yet another preferred embodiment, the individual detectors may be low-cost OES emitter/receivers. In an alternative embodiment, detection system 24 may comprise a single detector which is movable in a direction parallel to array axis 6.

Figure 2A:
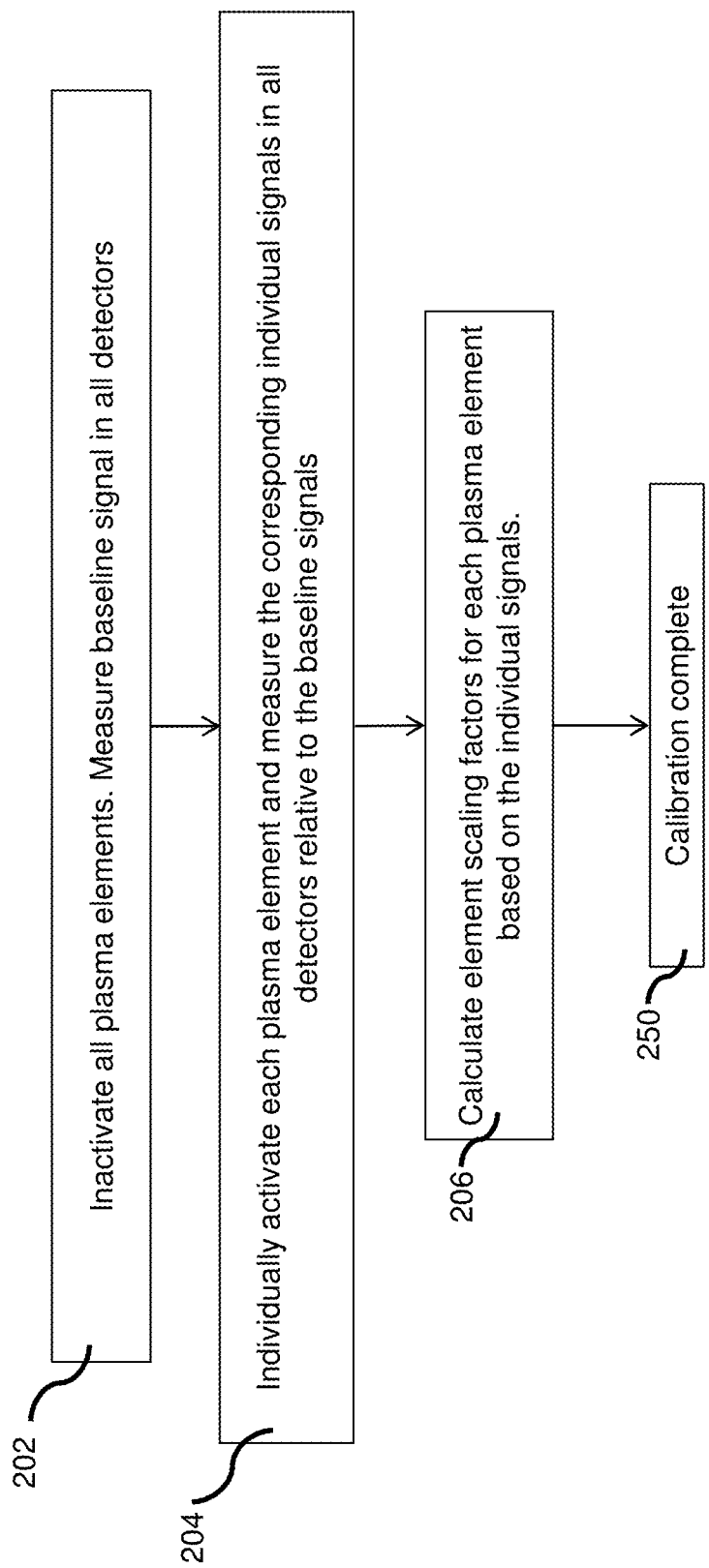
FIG. 2A is a flowchart illustrating the steps of a method of calibrating the output of elements of a plasma array.

FIG. 2A is a flowchart illustrating the steps of a method of calibrating the output of all plasma elements. In step 202 all plasma elements are inactivated with respect to reactive species output by turning off plasma power supplies or by shutting off reactive gas supply, but with carrier gas still flowing. A measurement is then made of a baseline signal without reactive species from longitudinal detectors 4 and 5 or transverse detection system 24. Step 202 enables future subtraction of background detector signals due to noise or zero offset. In step 204 each plasma element is sequentially and individually activated, with all other elements being inactive, and the corresponding individual signals in all detectors are measured relative to the baseline signals. In step 206, element scaling factors are calculated for each plasma element based on its corresponding individual signal, wherein each element scaling factor is inversely proportional to the corresponding individual signal. For example, if the individual signal corresponding to a particular plasma element is 1% higher than other individual signals, then the scaling factor of that plasma element is a reduction of reactive species by 1%. Such reduction may be achieved by various means, such as reduction of reactive gas flow or reduction of plasma power. In an embodiment, the reduction is achieved by reducing the percent "on" time in an on/off switching modulation scheme. In this embodiment, the plasma element corresponding to the lowest individual signal would be assigned a percent "on" time of 100% and all other plasma elements would be assigned percent "on" times in inverse proportion to the respective individual signals relative to the lowest individual signal. Having calculated the element scaling factors, the calibration is complete at step 250. The element scaling factors are stored in a table in a computer memory and may be recalled and used for uniformity modulation whenever the plasma array is used for treatment of a surface. The purpose of the uniformity modulation is to achieve uniformity of output of reactive species along array axis 6. However, it should be noted that the method of FIG. 2A does not provide an independent calibration of the detector signals. Thus, it must be assumed that the relationship between the reactive species output of a plasma element and the corresponding detector signal is the same for all plasma elements.

Figure 2B:
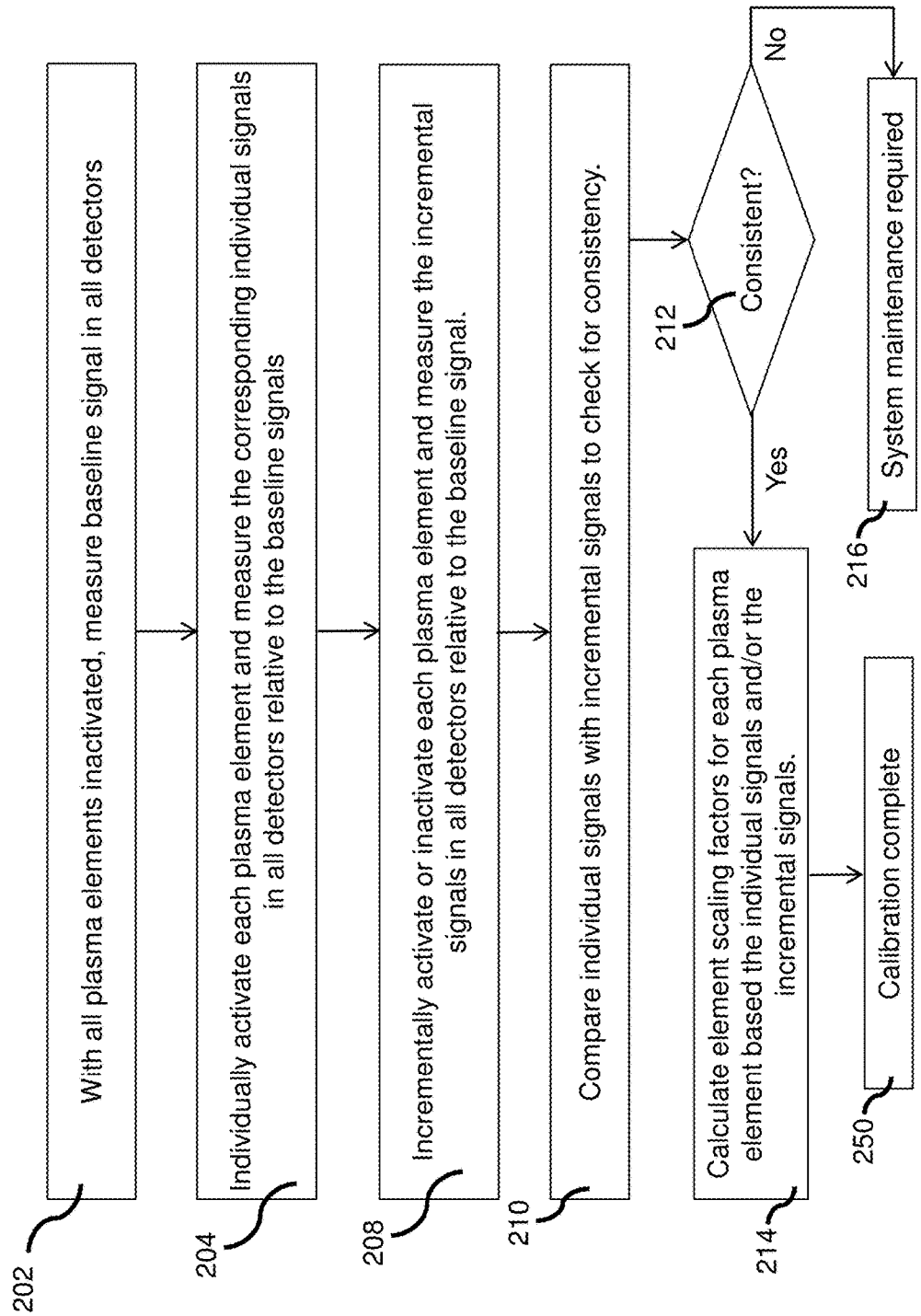
FIG. 2B is a flowchart illustrating the steps of an alternative method of calibrating the output of elements of a plasma array.

FIG. 2B is a flowchart illustrating the steps of an alternative method of calibrating the output of all plasma elements. In steps 202 and 204, baseline signals and individual signals are measured in the same way as in the method of FIG. 2A. In step 208 plasma elements are sequentially and incrementally activated, and the corresponding incremental signals in all detectors are measured relative to the baseline signals as each incremental plasma element is made active. Alternatively, in step 208, starting with all plasma elements activated, plasma elements may be sequentially and incrementally inactivated to measure the corresponding incremental signals, wherein the incremental signals are signal reductions. In step 210, the individual signals from step 204 and the incremental signals from step 208 are compared. If superposition of reactive species from each of the plasma elements is linear, then the individual signals and the incremental signals should be equal. In step 212, a consistency check is performed wherein the individual signals and the incremental signals are tested against a predetermined consistency criterion. For example, the consistency criterion may be based on the average error, standard deviation of the mean or any other suitable statistical criterion. If the consistency criterion is not satisfied in step 212, this is an indication that system maintenance is required in step 216, after which the consistency check of step 212 should be repeated. If the consistency criterion is satisfied in step 212, then in step 214 element scaling factors are applied to each plasma element based on the individual signals and/or the incremental signals. The scaling factors may be applied for uniformity modulation of plasma elements by any of the methods described in connection with step 206 of FIG. 2A, and may, for example, be based on the average of the individual signal and incremental signal corresponding to each plasma element. Note that, as for the method of FIG. 2A, the method of FIG. 2B does not provide an independent calibration of the detector signals.

Figure 2C:
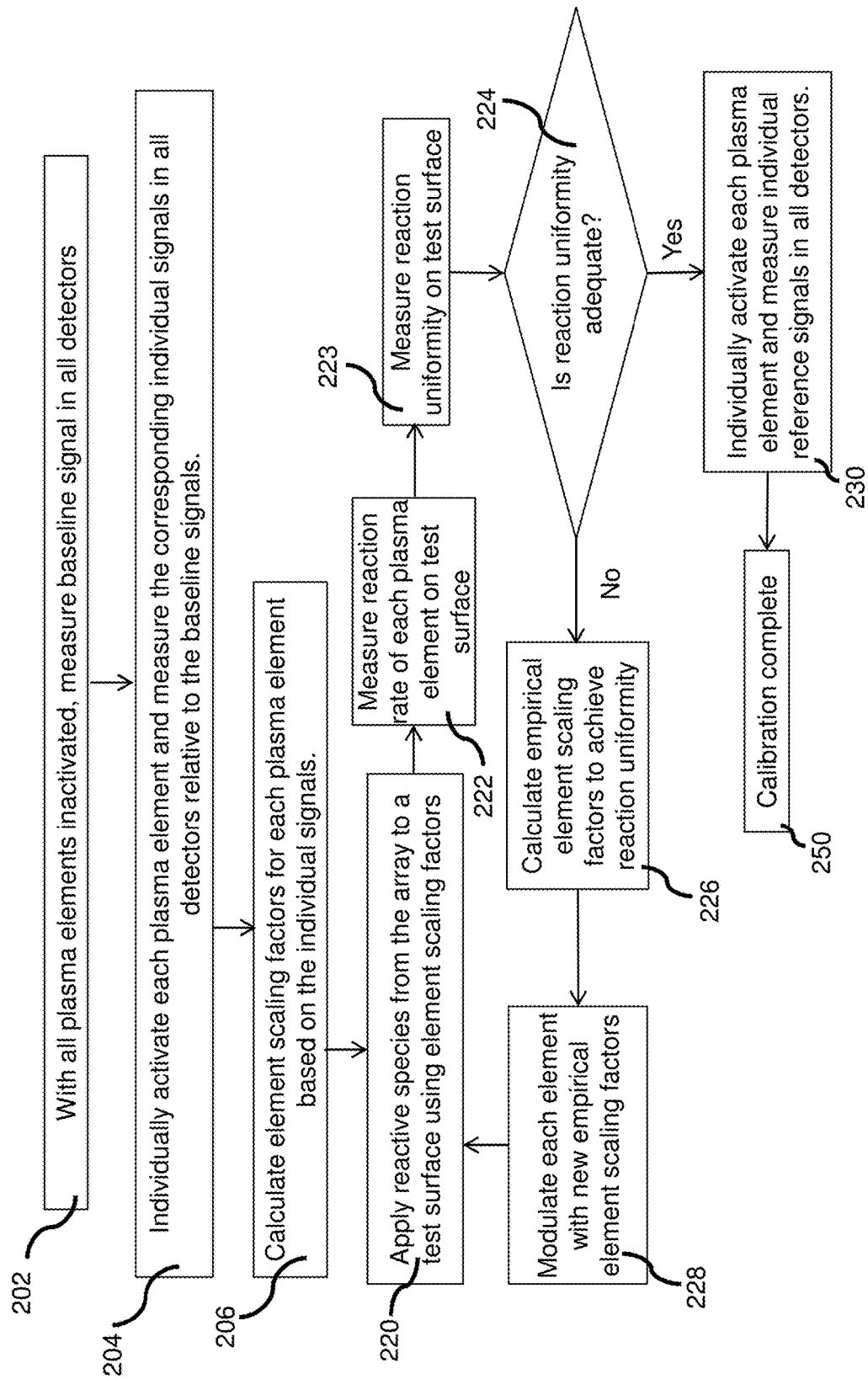
FIG. 2C is a flowchart illustrating the steps of an alternative calibration method which incorporates an empirical calibration.

FIG. 2C is a flowchart illustrating the steps of a preferred embodiment of a method to calibrate the output of all plasma elements. In steps 202, 204 and 206, baseline signals and individual signals are measured and element scaling factors are calculated in the same way as in the method of FIG. 2A. In step 220 reactive species from each plasma element are applied to a test surface using the element scaling factors calculated in step 206, and in step 222 the reaction rate of the reactive species on the test surface is measured for each plasma element. The reaction rate, as measured for example by the etch rate of a film on the test surface, may be directly correlated with the number of reactive species in the plasma (reactive species/cm/sec). The purpose of steps 220 and 222 is to empirically calibrate the relationship between reactive species output and detector signal by measuring the reaction rate of the reactive species with the test surface. This is a direct measurement of a surface effect of the reactive species, rather than a detector signal measurement of reactive species within the plasma, as is the case with, for example, FTIR and OES measurements. The material of the test surface is chosen to react in an easily quantifiable way with the reactive species, and the reaction rate is measured by methods which are described in connection with FIG. 3A below. Also, in step 222, adequacy of the reaction rate is compared with a rate criterion based on the time needed to achieve a predetermined total dose at a treatment surface. If the reaction rate measured at step 222 is not adequate, then parameters of the plasma elements, such as reactive gas flow and/or power, must be modified to increase the reaction rate, and the empirical calibration procedure should be repeated.

In step 223 the reaction uniformity is measured by comparing reaction rates as a function of positions on the test surface in a direction parallel to array axis 6. In step 224 the uniformity of the reaction along array axis 6 is compared to a predetermined statistical uniformity criterion such as standard deviation. If the uniformity criterion is not satisfied in step 224, then in step 226 empirical element scaling factors are calculated. The empirical element scaling factors are based on the reaction rates as function of positions along array axis 6 as measured in step 223. In order to achieve uniform reaction rate along array axis 6, the empirical element scaling factor of each plasma element is calculated to be inversely proportional to the reaction rate at the corresponding position of the plasma element along array axis 6. In step 228 each plasma element is modulated with the new empirical element scaling factors calculated in step 226. The empirical test beginning in step 220 is then repeated using uniformity modulation with the updated empirical element scaling factors until the uniformity criterion is satisfied in step 224. If the uniformity criterion is satisfied in step 224, then in step 230 each plasma element is sequentially and individually activated, with all other elements being inactive, and corresponding individual reference signals in all detectors are measured relative to the baseline signals. Calibration is complete at step 250 and the element scaling factors used in step 220 and the individual reference signals measured in step 230 are stored in a table in a computer memory and may be recalled and used whenever the plasma array is used for treatment of a surface.

Application of the empirical scaling factors for uniformity modulation may be achieved by "on/off" modulation, by power supply modulation or by reactive gas flow modulation. When using "on/off" modulation, the plasma element corresponding to the lowest reaction rate in step 222 would be assigned a percent "on" time of 100% and all other plasma elements would be assigned percent "on" times in inverse proportion to their respective reaction rates relative to the lowest reaction rate. When using power supply or gas flow modulation, the power setting or gas flow setting of each plasma element would correspond to the settings used in step 228 of FIG. 2C which result in adequate uniformity in step 224.

The empirical method of FIG. 2C is an empirical calibration of the output of all plasma elements, and may be performed once for each set of operational parameters of plasma array 2. Alternatively, the empirical calibration may be performed periodically to ensure consistency of all treatment parameters. During treatment, the empirical element scaling factors may be used to provide a repeatable surface treatment with the same operational parameters as used in the empirical calibration. The individual reference signals from longitudinal detectors 4 and 5 or transverse detection system 24, as measured in step 230, may be used to provide a check for consistency of the calibration. Thus, prior to a treatment, the individual signals are measured and compared with the reference signals. The individual signals should be the same as the reference signals to within a predetermined consistency criterion. If the consistency criterion is not satisfied, the empirical calibration may be repeated.

Figure 3B:
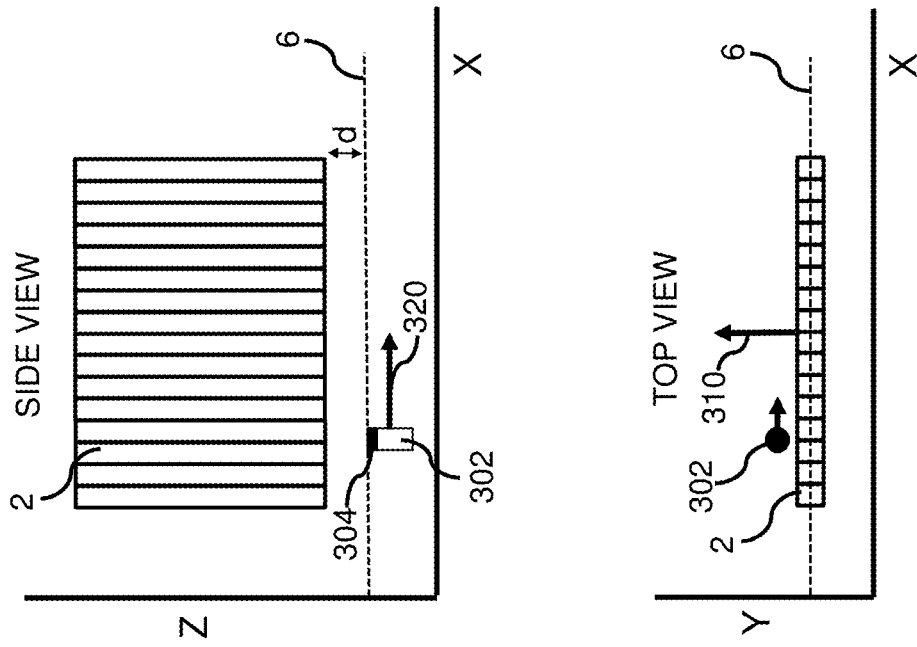
FIG. 3B is a schematic illustration showing top and side views of a system for empirical calibration of reactive species using a movable point probe.
Figure 3A:
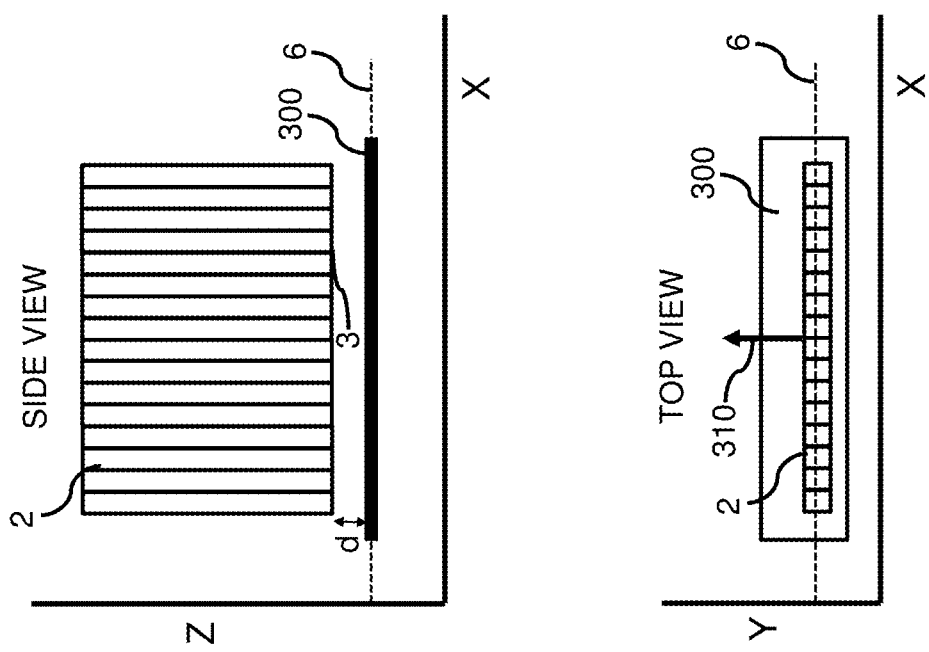
FIG. 3A is a schematic illustration showing top and side views of a system for empirical calibration of reactive species by scanning a plasma array over a test surface.

FIG. 3A is a schematic illustration of a system for empirical calibration of plasma array 2 using a test surface 300 over which plasma array 2 is mechanically scanned in a scan direction 310 which is orthogonal to array axis 6. In FIG. 3A a top view is represented in a XY plane, and a side view is represented in a XZ plane. An output plane 3 of plasma array 2 is separated from test surface 300 by a distance d in the Z direction, such that reactive species output from plasma array 2 (not shown) is incident upon test surface 300. Test surface 300 reacts in an easily quantifiable way with reactive species from plasma array 2. Test surface 300 may be of a material that is etched (for example, carbon or a carbon compound such as polyimide). Alternatively, the material of test surface 300 may be oxidized or nitrided by the reactive species. Other forms of reaction between reactive species and test surface 300 may be devised, and all are within the scope of the present disclosure. The rate of reaction (such as etching, oxidation or nitridation) may be quantified using the exposure time and a measurement of the loss or gain of material at test surface 300 or by a measurement of the thickness of a film, such as oxide or nitride, formed on test surface 300 during the reaction. In one embodiment, test surface 300 comprises a film of a carbon-containing material at a well-defined temperature, and the reaction rate is measured by means of a film thickness measurement using methods known in the art. The measured reduction in thickness of the film quantifies the reactive species exposure and the uniformity of the thickness loss quantifies the uniformity of exposure over the measurement area.

FIG. 3B represents an alternative system for empirical calibration of plasma array 2. The empirical calibration uses a movable point probe 302 over which plasma array 2 is mechanically scanned in orthogonal scan direction 310. Movable point probe 302 is used to determine the rate and uniformity of reactive species exposure. Movable point probe 302 determines the reactive species exposure at one position along array axis 6 by integrating the exposure as plasma array 2 is scanned in orthogonal scan direction 310. Movable point probe 302 is then translated in a motion direction 320, parallel to array axis 6, to a new position along array axis 6. Plasma array 2 is then again scanned in orthogonal scan direction 310, and the integrated exposure measurement is repeated. Repeating this procedure for all positions of movable point probe 302 along array axis 6 results in both a rate and uniformity determination necessary to calibrate the reactive species output of plasma array 2. In an embodiment, movable point probe 302 may comprise a fixed temperature quartz crystal microbalance (QCM) sensor which makes in situ measurements of the reaction rate by directly measuring change of mass of a surface coating 304 on the QCM sensor. In an embodiment, surface coating 304 may comprise a thin film such as a carbon film, and mass loss of the thin film may be measured by the QCM sensor in real time.

Figure 3C:
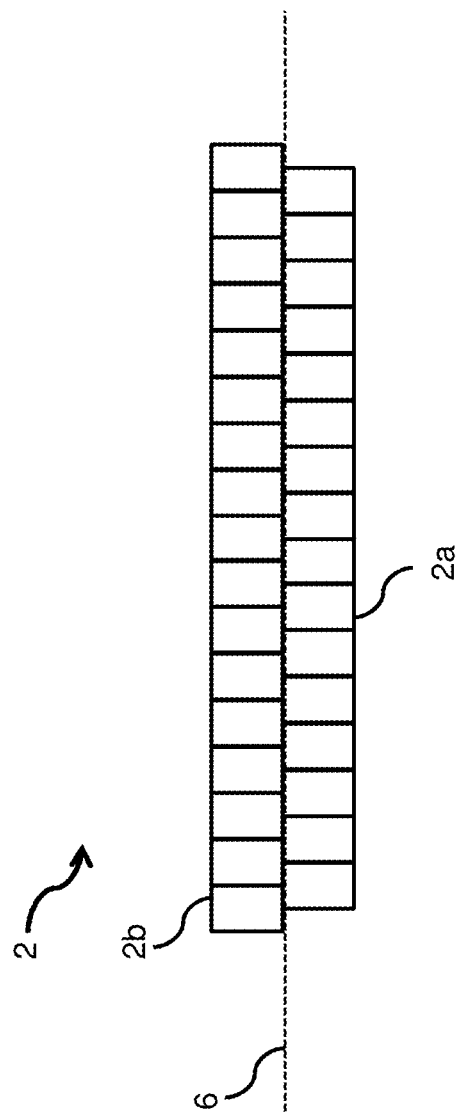
FIG. 3C illustrates an embodiment of a plasma array comprising two individual plasma arrays.

If the reactive species output of each plasma element is strongly peaked at its centerline, reactive species output along array axis 6 may exhibit oscillations peaked at each centerline, making it more difficult to meet the uniformity criterion. FIG. 3C illustrates an embodiment in which plasma array 2 comprises two individual plasma arrays 2a and 2b, wherein the individual plasma arrays 2a and 2b are configured side by side, but displaced by half the width of each plasma element in a direction parallel to array axis 6. The arrangement of FIG. 3C may exhibit superior uniformity. More than two individual plasma arrays may be stacked in similar manner.

Figure 4:
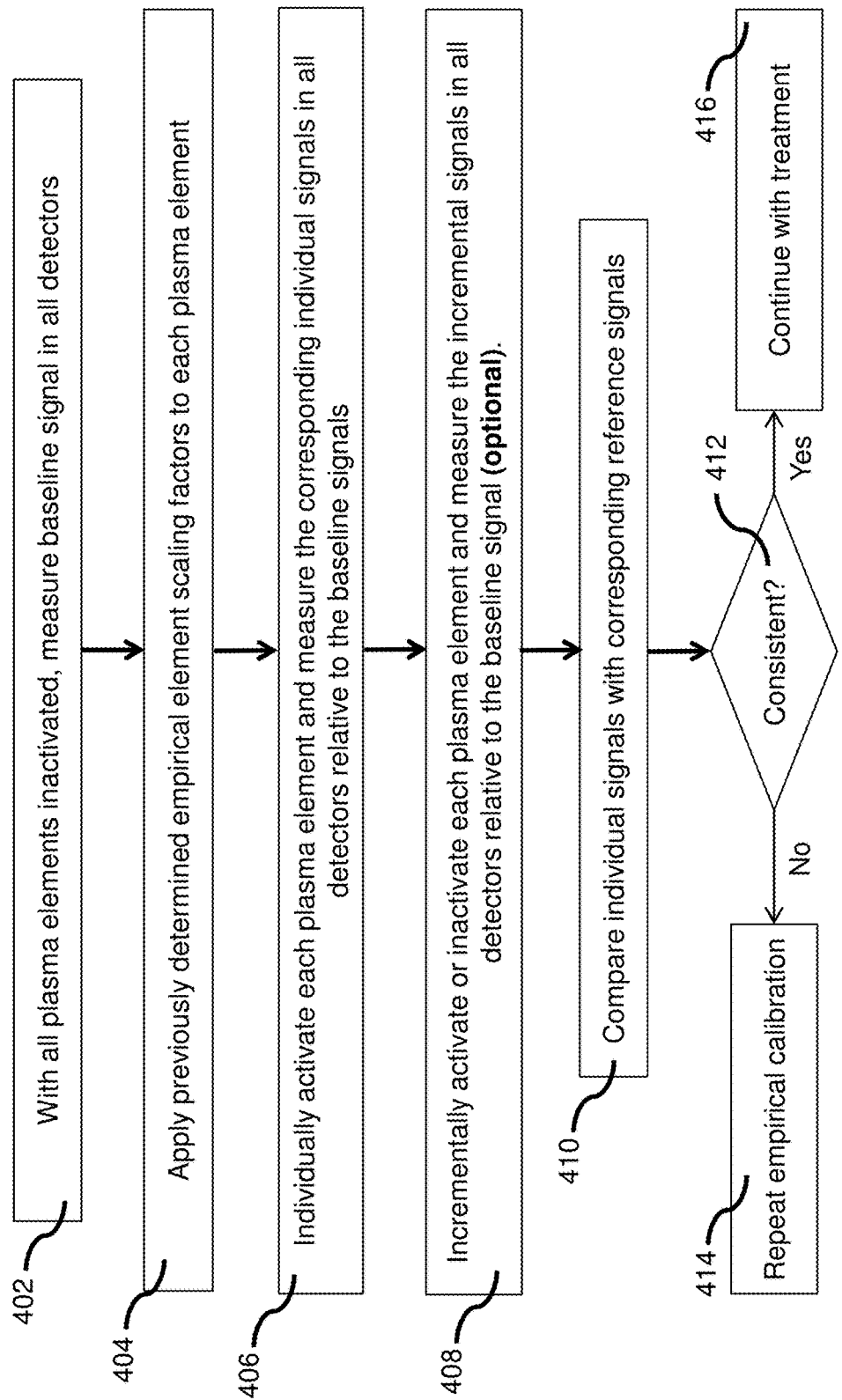
FIG. 4 is a flowchart illustrating the steps of a method of verifying normal operation of the plasma array and detectors prior to a treatment procedure.

FIG. 4 is a flowchart illustrating the steps of a checking method performed prior to a surface treatment. The purpose of the checking method is to verify that plasma array 2 and longitudinal detectors 4 and 5 or transverse detection system 24 are operating normally. In step 402 all plasma elements are inactivated with respect to reactive species output by turning off plasma power supplies or by shutting off reactive gas supply, but with carrier gas still flowing. A measurement is then made of a baseline signal without plasma from all detectors. In step 404 previously determined empirical element scaling factors are applied to determine uniformity modulation of each plasma element. Application of empirical scaling factors should provide a uniform reactive species output distribution across plasma array 2 with a calibrated reaction rate, and steps 406 to 416 are a consistency check to ensure that the empirical calibration is still valid. In step 406 each plasma element is sequentially and individually activated, with uniformity modulation in accordance with the corresponding empirical element scaling factors and with all other elements being inactive. Corresponding individual signals in all detectors are measured relative to the baseline signals. Step 408 is an optional step in which plasma elements are sequentially and incrementally activated or inactivated with uniformity modulation in accordance with the corresponding empirical element scaling factors, and the corresponding incremental signals in all detectors are measured relative to the baseline signals as each incremental plasma element is made active or inactive. Step 408 includes a detector consistency check wherein the individual signals and the incremental signals are tested against a predetermined detector consistency criterion. In step 410 individual signals (or a combination of individual signals and incremental signals) are compared with corresponding reference signals measured in step 230 of FIG. 2C. The individual signals and the incremental signals should match to within a predetermined reference consistency criterion, which may be any appropriate statistical measure of the deviation of the signals. In step 412 a consistency check is performed against the reference consistency criterion. If the reference consistency criterion is satisfied, treatment may continue in step 416. If the reference consistency criterion is not satisfied, the empirical calibration may be repeated in step 414.

FIGS. 5A, 5B, 5C and 5D are schematic illustrations of a system and method for deriving a dose modulation for attaining a predetermined dose distribution of reactive plasma species within a predetermined treatment area.

Figure 5A:
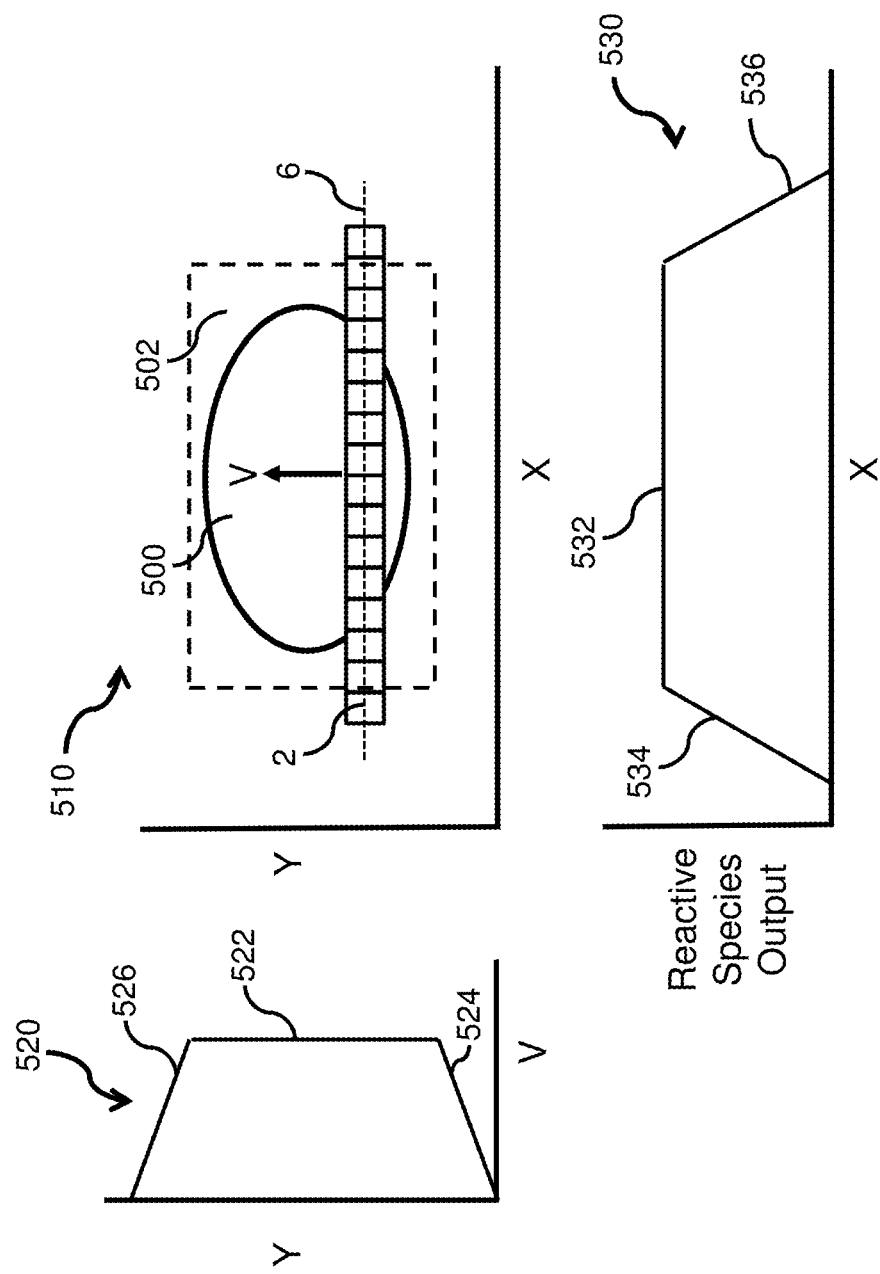
FIG. 5A is a schematic illustration showing scanning of a plasma array with uniformity modulation to attain a uniform distribution of reactive plasma species within a rectangular area.

Diagram 510 in FIG. 5A shows a top view in the XY plane of plasma array 2 being scanned at a scan velocity V in the Y direction over a predetermined treatment area 500. For simplicity of explanation, treatment area 500 is shown as an ellipse, but treatment area 500 can have any shape, including irregular shapes, and all such shapes are within the scope of the present disclosure. Diagram 520 in FIG. 5A shows a graph of scan velocity V as a function of position Y in the scan direction. It can be seen that diagram 520 has an accelerating portion 524, a constant velocity portion 522, and a decelerating portion 526. Note that the extent of constant velocity portion 522 in the Y dimension is larger than the largest extent of treatment area 500 in the Y dimension. Note also that, having come to rest at the end of decelerating portion 526, the scan may reverse direction, so that portion 526 becomes an accelerating portion and portion 524 becomes a decelerating portion. Thus, plasma array 2 may be scanned back and forth multiple times.

Diagram 530 in FIG. 5A shows a graph of reactive species output from plasma array 2 as a function of position X orthogonal to the scan direction and parallel to array axis 6. It can be seen that diagram 530 has a uniform reactive species output portion 532, and non-uniform portions 534 and 536 where the reactive species output falls to zero on either side of plasma array 2. The uniformity of reactive species output in portion 532 is the result of the uniformity modulation and calibration methods described above in connection with FIGS. 2 and 3. Note that the extent of uniform reactive species output portion 532 in the X dimension is larger than the largest extent of treatment area 500 in the X dimension. A rectangular area 502 in diagram 510 delineates the boundaries of constant velocity portion 522 in the Y dimension and uniform reactive species output portion 532 in the X dimension. Therefore, a uniform distribution of reactive species is delivered within the boundaries of rectangular area 502.

Figure 5B:
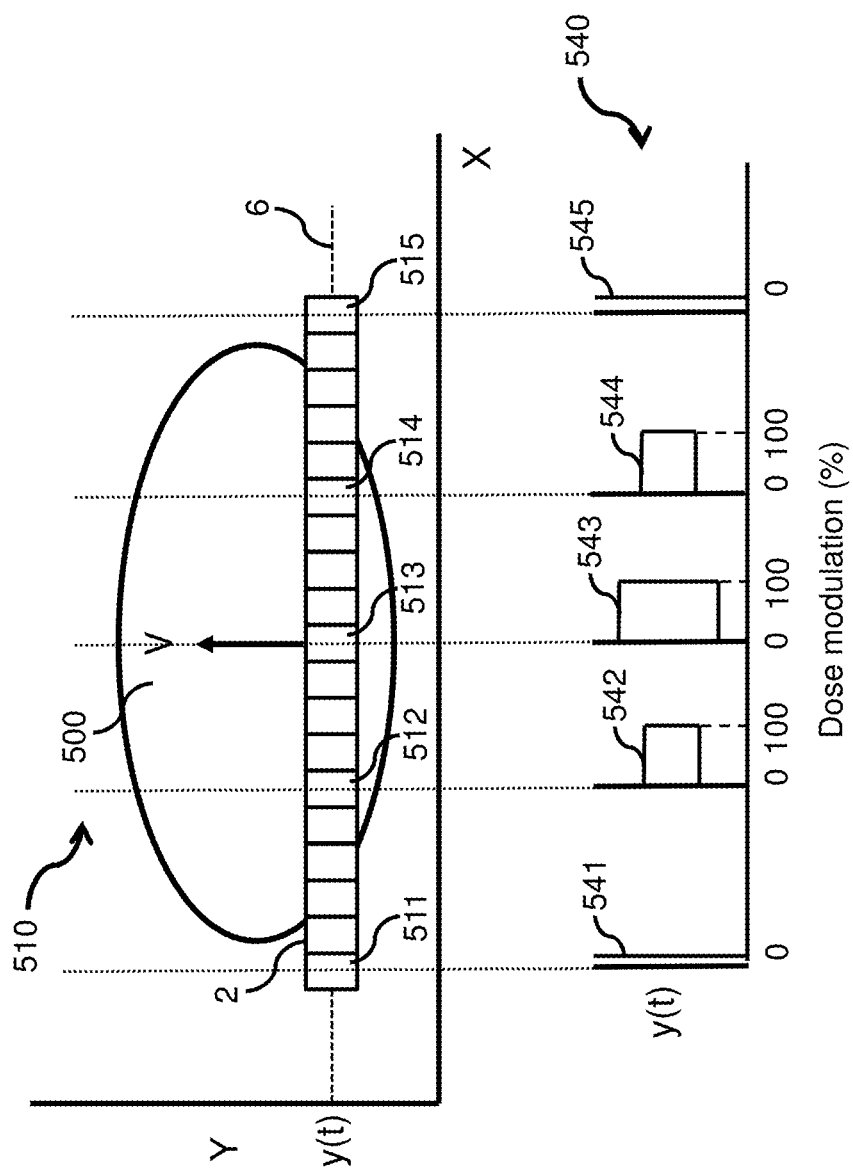
FIG. 5B is a schematic illustration showing scanning of a plasma array with uniformity and dose modulation of the plasma elements to attain a uniform distribution of reactive plasma species within a predetermined treatment area of any shape.

In FIG. 5A, exposure to reactive species output is uniform within rectangular area 502, which is larger than treatment area 500. In fact, the total area of exposure to reactive species output is larger than rectangular area 502, because exposure due to portions 524, 526, 534 and 536 must also be taken into account. Such exposure outside desired treatment area 500 may be unacceptable in many biological applications, such as wound treatment. FIG. 5B illustrates a dose modulation method according to the present disclosure in which the area of treatment with plasma may correspond exactly to desired treatment area 500.

Diagram 510 in FIG. 5B shows a Y location y(t) of array axis 6 at a time t as plasma array 2 is scanned across treatment area 500. For purposes of explanation, attention is drawn to representative plasma elements 511, 512, 513, 514 and 515, although it is to be understood that the explanation for the representative plasma elements is valid for all plasma elements of plasma array 2. Diagram 540 in FIG. 5B shows graphs of a percent dose modulation of each plasma element as a function of y(t), wherein the percent dose modulation is the percent of time that a plasma element is "on" with respect to reactive species output.

Diagram 540 comprises graphs 541, 542, 543, 544 and 545, each graph showing the percent dose modulation for plasma elements 511, 512, 513, 514 and 515 respectively. Graphs 541, 542, 543, 544 and 545 illustrate the method of dose modulation by turning the respective plasma elements on and off at various times during the scan of plasma array 2 across treatment area 500. During scanning of plasma array 2, plasma elements 511 and 515 do not intersect treatment area 500, and therefore corresponding graphs 541 and 545 show that the dose modulation is 0% throughout the scan, meaning that plasma elements 511 and 515 are not activated. On the other hand, plasma element 513 traverses treatment area 500 at its maximum dimension in the Y direction, and therefore corresponding graph 543 shows 100% dose modulation for the longest period during the scan. Dose modulation of element 513 is 100% when its reactive species output is coupled with treatment area 500, and dose modulation of element 513 is 0% when its reactive species output is outside of treatment area 500. Plasma elements 512 and 514 traverse treatment area 500 at X locations where its dimension in the Y direction is less than the maximum, and therefore corresponding graphs 542 and 544 show 100% dose modulation for a shorter period during the scan. Thus, by following a similar procedure for all plasma elements of plasma array 2, each plasma element may be activated when its reactive species output is coupled to treatment area 500, and inactivated when its reactive species output is outside of treatment area 500. Consequently, there will be uniform reactive species output at all locations within treatment area 500 and zero reactive species output at all locations outside of treatment area 500.

Activation and inactivation of reactive species output from plasma elements for dose modulation may be achieved by various methods. In a preferred embodiment, plasma elements may be inactivated by closing a gas valve to cut off flow of reactive gas. In another preferred embodiment, plasma elements may be inactivated by turning off an appropriate power supply. It should be noted that, since dose modulation occurs on the time scale of a mechanical scan of plasma array 2, (0.1 to 10 seconds per scan), switching of plasma elements for dose modulation may be achieved at a time scale about 100 times shorter (1 to 100 milliseconds).

Note that plasma treatment of treatment area 500 may not be completed in a single scan. Multiple scans of plasma array 2 back and forth may be required achieve a desired total treatment dose. Note also that designation of "100%" modulation for a plasma element in FIG. 5B is understood to mean that the modulation is 100% with respect to the corresponding uniformity modulation as defined by the corresponding empirical element scaling factor. Thus, if, for example, the empirical calibration has determined that a particular plasma element has 10% excess output relative to the lowest output plasma element, then 100% modulation in graph 540 may correspond to 90% "on" time.

Figure 5C:
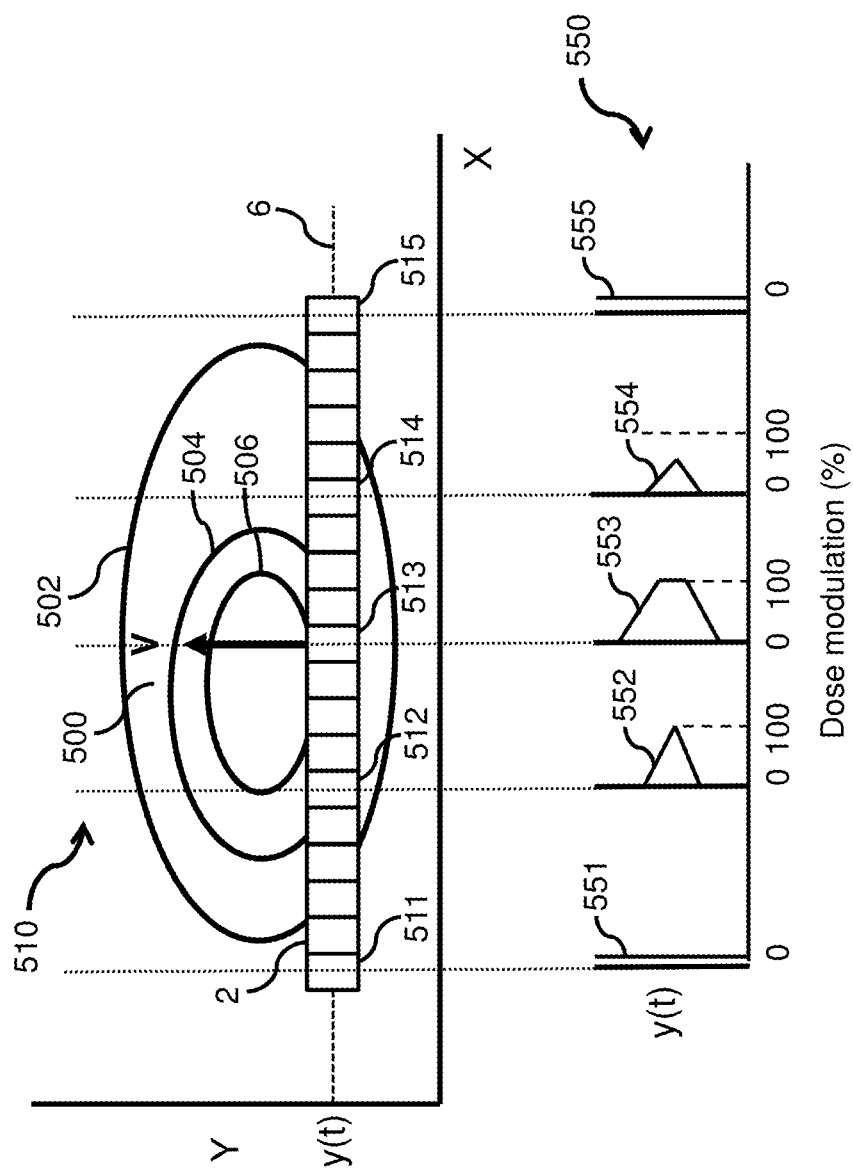
FIG. 5C is a schematic illustration showing scanning of a plasma array with uniformity and dose modulation of the plasma elements to attain a predetermined contour dose distribution of reactive plasma species within a predetermined treatment area of any shape.

In the method of FIG. 5B, a uniform dose is delivered to all locations within treatment area 500. FIG. 5C illustrates a method of dose modulation according to the present disclosure in which a predetermined non-uniform dose distribution may be delivered within treatment area 500. The desired dose distribution is defined by means of a contour dose map in the XY plane. For purposes of explanation, a simplified contour dose map is illustrated in FIG. 5C, but the method described is generally applicable to a contour dose map of any kind. In FIG. 5C the contour dose map of treatment area 500 is defined by three contour ellipses 502, 504, and 506. By way of example, the dose within ellipses 502 and 504 is assumed to be rising towards the central parts of each ellipse, while the dose within ellipse 506 is assumed to be constant at a maximum value. A diagram 550 comprises graphs 551, 552, 553, 554 and 555, each graph showing the percent dose modulation for plasma elements 511, 512, 513, 514 and 515 respectively. As plasma array 2 as scanned across treatment area 500, plasma elements 511 and 515 do not intersect treatment area 500, and therefore corresponding graphs 551 and 555 show that the dose modulation is 0% throughout the scan. Plasma element 513 traverses all three contour ellipses 502, 504 and 506, and corresponding graph 553 shows rising dose modulation as element 513 traverses rising dose requirements of contour ellipses 502 and 504, constant 100% dose modulation as element 513 traverses constant dose requirement within contour ellipse 506, and falling dose modulation as element 513 traverses falling dose requirements of contour ellipses 504 and 502. Plasma element 512 traverses contour ellipses 502 and 504, reaching the boundary of contour ellipse 506, and graph 552 shows the corresponding rising and falling modulation, with the peak modulation reaching 100% at y(t) corresponding to the boundary of contour ellipse 506. Plasma element 514 traverses only contour ellipse 502, and graph 554 shows the corresponding rising modulation, peaking near the center of contour ellipse 502 and falling thereafter. Note that the peak dose modulation in graph 554 is less than 100% because reactive species from element 514 are never coupled with the area within contour ellipse 506 having the maximum dose requirement.

Figure 5D:
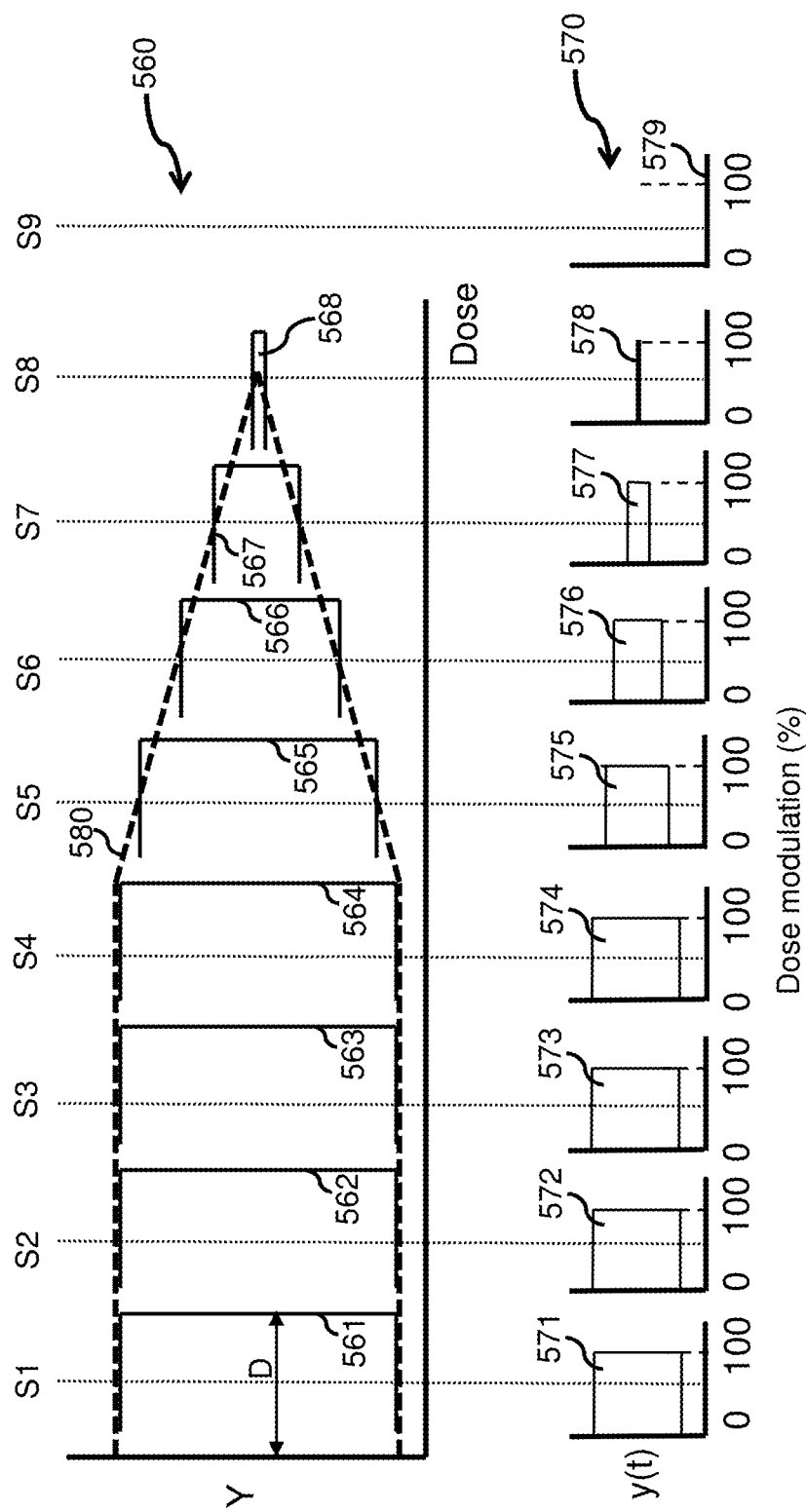
FIG. 5D schematically illustrates modulation of a single plasma element over multiple scans in order to attain a required dose distribution.

The method illustrated in FIG. 5C allows treatment within treatment area 500 with treatment dose characterized by a predetermined contour distribution. However, the method assumes that the required dose may be achieved with a single scan, which is usually not the case. FIG. 5D illustrates dose modulation of a single plasma element, such as plasma element 512 of FIG. 5C, wherein multiple scans of plasma array 2 are required to achieve the required dose even at the low-dose boundary of contour ellipse 502. Diagram 560 in FIG. 5D shows graphs of dose as a function of Y, at a position on array axis 6 corresponding to the position of plasma element 512. Diagram 570 in FIG. 5D shows graphs of plasma element modulation as a function of y(t). Required dose graph 580 is a graph of the total required dose as a function of Y at the X-position of plasma element 512. Dose graph 561 shows the dose D obtained from a first scan S1 of plasma array 2 and dose modulation graph 571 shows the corresponding dose modulation of plasma element 512. Since plasma element 512 is at 100% dose modulation for all parts of scan S1 which are within treatment area 500, dose D is the maximum dose that can be delivered in a single scan. In subsequent scans S2, S3 and S4, accumulation of dose is shown in dose graphs 562, 563 and 564, and corresponding dose modulation graphs 572, 573 and 574 show 100% dose modulation throughout for all parts of each scan which are within treatment area 500. At scan S5, dosing is complete for small and for large values of Y, so that dose graph 565 and dose modulation graph 575 have smaller extent in the Y-direction. For scans S6, S7 and S8, dose graphs 566, 567 and 568, and dose modulation graphs 576, 577 and 578, show decreasing extent in the Y-direction in accordance with required dose graph 580. At scan S9, the dose requirement has been completely fulfilled, so that the dose modulation of plasma element 512 is 0% throughout scan S9, as shown in dose modulation graph 579.

The method described in FIG. 5D is applied simultaneously to all plasma elements of plasma array 2 in order to accumulate the required contour dose distribution within treatment area 500. Note that the number of 9 scans illustrated in FIG. 5D is for exemplary purposes only. The actual number of scans for a treatment will be calculated based on the total required dose and the dose per scan D for each plasma element.

FIGS. 5E and 5F illustrate examples of combined uniformity modulation and dose modulation of a single plasma element. By way of example, uniformity and dose modulations are illustrated for dose graph 571 of FIG. 5D, corresponding to scan S1 of plasma element 512. Again by way of example, it is assumed that the empirical element scaling factor of element 512 requires a uniformity modulation of 90%. In FIGS. 5E and 5F, dose graph 571 is an envelope to a series of faster "on/off" pulses implementing the uniformity modulation of 90%. In FIG. 5E, "on" pulses have a time duration of 90% and "off" pulses have a time duration of 10%. In FIG. 5F there is a series of pulses of equal duration, but with every tenth pulse being omitted. Other methods of incorporating uniformity modulation with an envelope of dose modulation may be devised, and all are within the scope of the present disclosure. Note that, in order to implement uniformity modulation within an envelope of dose modulation, pulse rise and fall times may be in the range of 10 microseconds to 1 millisecond.

Figure 6:
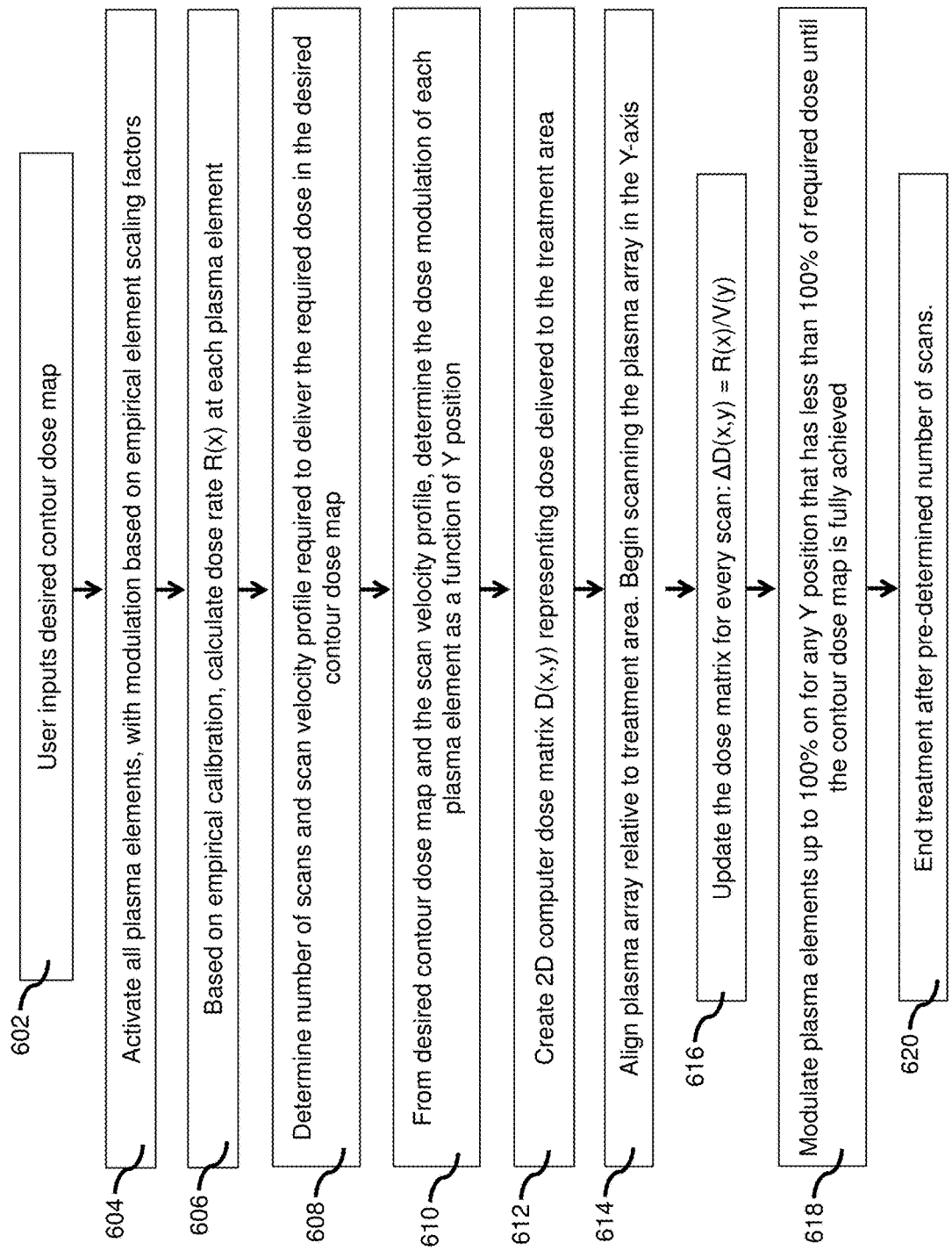
FIG. 6 is a flowchart illustrating the steps of a method of delivering reactive plasma species to a predetermined treatment area in accordance with a predetermined contour dose map.

FIG. 6 is a flowchart illustrating the steps of a method of delivering reactive plasma species to treatment area 500 in accordance with a predetermined contour dose map. In step 602 the desired XY contour dose map is input by a user or by some other automated means. In step 604 all plasma elements of plasma array 2 are activated with uniformity modulations based on empirical element scaling factors determined in step 226 of FIG. 2C. Step 226 may also incorporate the consistency checking method described in connection with FIG. 4. Reactive species output from plasma array 2 should match reactive species output profile 530 shown in FIG. 5A. In step 606, based on the empirical reaction rate measurements of step 222 in FIG. 2C, a dose rate R(x) is calculated for each plasma element, wherein R(x) is in units of number of reactive species/cm/sec. In step 608, a mechanical scan velocity profile is determined as shown in graph 520 of FIG. 5A, and a number of scans, N, required to deliver the desired total dose within the contour dose map is determined based on the relationships:

$$\Delta D(x, y) = R(x)/V(y) \quad (1)$$

$$N = D_{max}/\Delta D_{max} \quad (2)$$

where $\Delta D(x,y)$ is the dose increment per scan, V(y) is the scan velocity, $D_{max}$ is the maximum dose at a maximum dose point within the contour dose map and $\Delta D_{max}$ is the dose per scan for the plasma element corresponding to the maximum dose point.

In step 610 the dose modulation of each plasma element is determined based on the scan velocity profile and the contour dose map, using the methods described in connection with FIGS. 5A, 5B, 5C and 5D. In step 612, a two-dimensional computer dose matrix is created, wherein the dose matrix represents the dose D(x,y) delivered to treatment area 500. In step 614, plasma array 6 is aligned relative to treatment area 500, with a predetermined distance d between output plane 3 of plasma array 2 and treatment area 500, as shown in FIG. 3A. Scanning of plasma array 6 in the Y-direction is commenced, and in step 616, the dose matrix is updated with the dose increment $\Delta D(x,y)$ at every scan in accordance with equation (1). In step 618, as described in connection with FIG. 5D, each plasma element is dose modulated at up to 100% at each scan for any Y position that has not yet achieved 100% of the required dose. Variations in required dose along the Y scan direction are accounted for by variation of the percent dose modulation as described in connection with diagram 570 of FIG. 5D. The plasma treatment ends at step 620 when the pre-determined number of scans, N, has been completed and the dose matrix corresponds to the desired contour dose map.

In an alternative embodiment of the method of FIG. 6, plasma array 2 may be scanned in conjunction with a plasma applicator comprising one or more position sensors to measure the position, orientation and velocity of plasma array 2 relative to treatment area 500. In this embodiment, motion of plasma array 2 may be arbitrary, such as during handheld operation, and dose applied to treatment area 500 may be computed using an empirical lookup table comprising a table of element scaling factors as a function of the distance d and the orientation of plasma array 2 relative to the plane of treatment area 500. In step 606, dose rate R(x) is calculated based on the empirical lookup table and the distance d and orientation of plasma array 2, as determined by the position sensors. In step 616, the dose matrix is updated at each scan by means of equation (1), wherein dose R(x) is calculated based on the empirical lookup table, and scan velocity V(y) is measured in real time by the position sensors. With this embodiment incorporating one or more position sensors, repeatable treatment with handheld scanning may be achieved regardless of who operates the system. Since there is feedback from the position sensors, repeatability of treatment is not dependent upon the uniformity of the manual scanning motion, unlike prior art systems which operate with no feedback.

Figure 7:
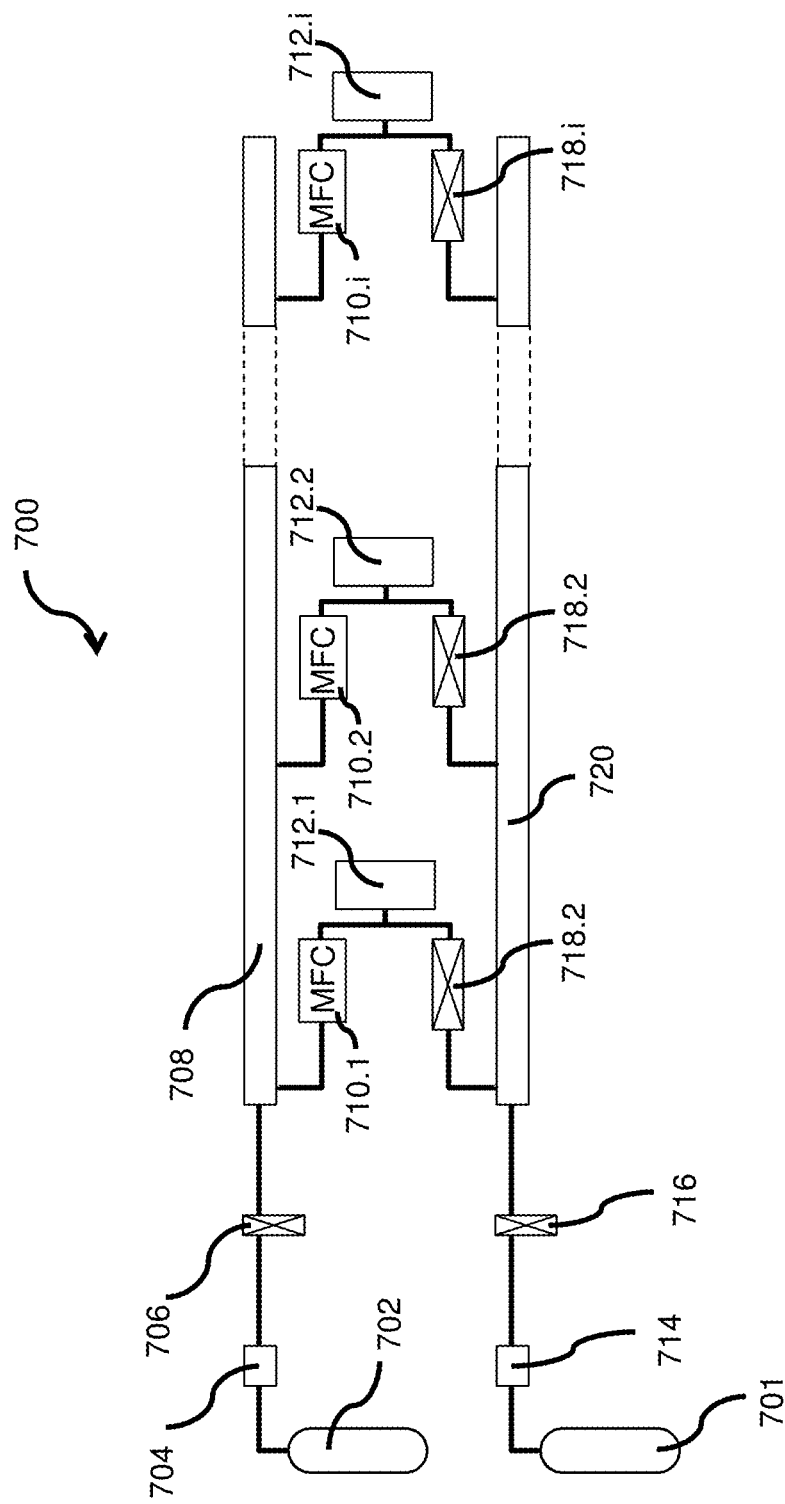
FIG. 7 is a schematic diagram of a gas distribution system for a plasma array allowing modulation of reactive gas flow to each plasma element.

FIG. 7 is a schematic diagram of an exemplary gas distribution system 700 for plasma array 2, providing the means by which flow of the reactive gas may be modulated for each plasma element. Gas distribution system 700 comprises a carrier gas supply 702, wherein the carrier gas is a non-reactive species such as Ar or He, and a reactive gas supply 701, wherein the reactive gas is a reactive species such as $O_2$ or $O_2/N_2$. Associated with carrier gas supply 702 is a pressure regulator 704, a gas valve 706, a gas plenum 708, and mass flow controllers 710.1, 710.2 . . . 710.$i$ to provide a constant carrier gas flow for plasma elements 712.1, 712.2 . . . 712.$i$ respectively. Associated with reactive gas supply 701 is a pressure regulator 714, a gas valve 716, and a constant pressure gas plenum 720 to provide a constant inlet pressure to fast gas valves 718.1, 718.2 . . . 718.$i$, each fast gas valve having a fixed gas conductance to plasma elements 712.1, 712.2 . . . 712.$i$ respectively. Thus, each plasma element is provided with a carrier gas and a reactive gas supply, the latter capable of being switched on or off very quickly during operation to modulate the flow of reactive species from each plasma array element. Note that other gas distribution systems may be devised and all are within the scope of the present disclosure.

Figure 8:
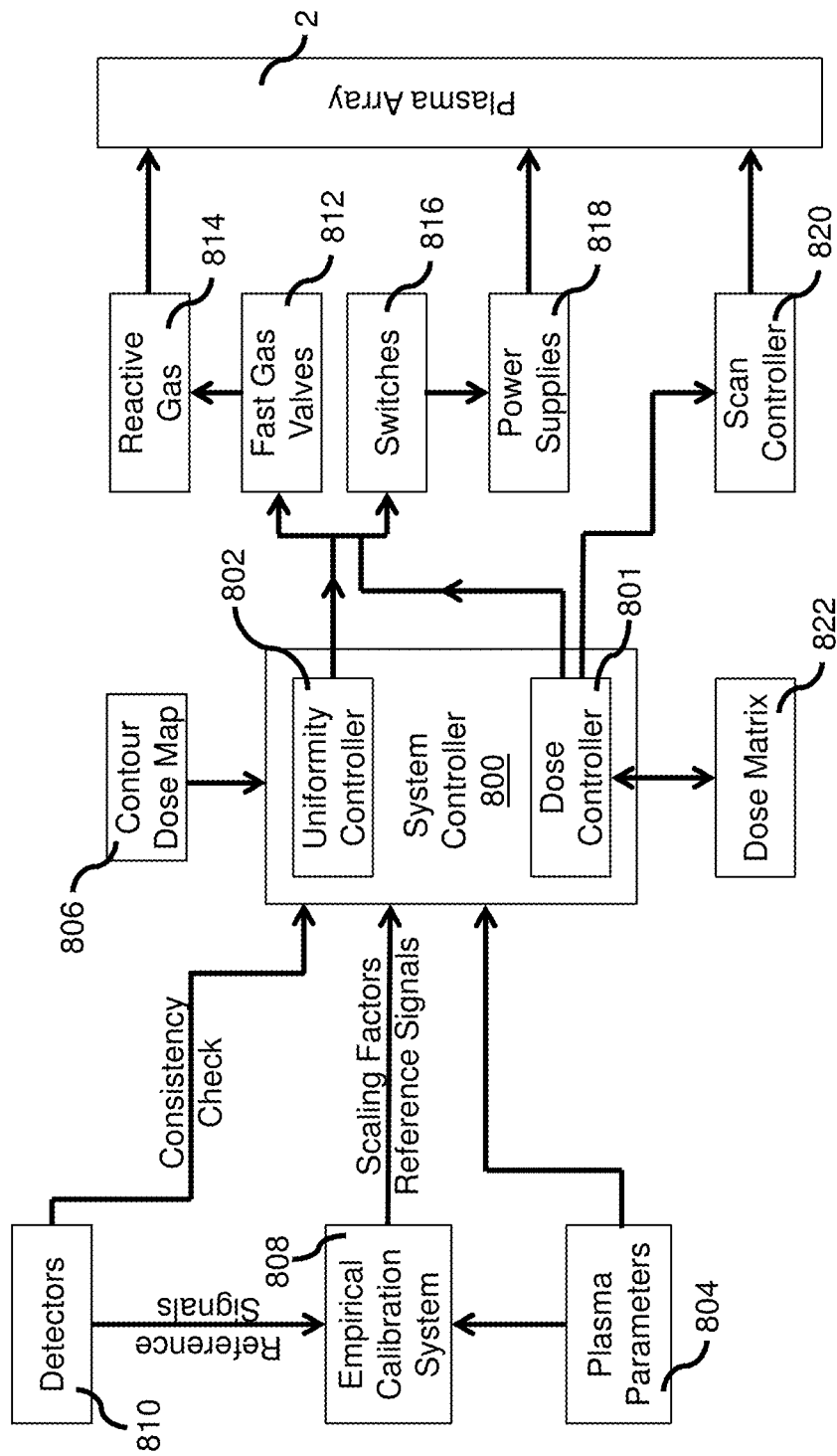
FIG. 8 is a schematic diagram of a system configured to deliver reactive plasma species to a predetermined treatment area in accordance with a predetermined contour dose map.

FIG. 8 is a schematic diagram of a system configured to deliver a predetermined dose distribution of reactive plasma species within a predetermined treatment area. The system comprises a system controller 800, system controller 800 further comprising a dose controller 801 and a uniformity controller 802. System controller 800 receives input of a contour dose map 806 which defines the boundaries and desired dose distribution within treatment area 500. System controller 800 also receives input of plasma parameters 804, wherein plasma parameters 804 define the types and flow rates of the carrier gas and reactive gas, and the settings of all power supplies required to power plasma array 2. Plasma parameters 804 are also input to an empirical calibration system 808. Empirical calibration system 808 is configured to perform empirical calibration of the reactive species output of plasma array 2 prior to use of plasma array 2 for a treatment. The empirical calibration is performed using plasma parameters 804 and results in an empirical scaling factor for uniformity modulation of each of the plasma elements of plasma array 2. After applying the uniformity modulation, empirical calibration system 808 derives individual reference signals from detectors 810. The empirical scaling factors and the reference signals are input to system controller 800. Prior to performing a treatment, system controller 800 activates the plasma elements with application of the empirical scaling factors for uniformity modulation, and may then perform a consistency check by comparing individual signals from detectors 810 to the reference signals.

During a treatment procedure, dose controller 801 and uniformity controller 802 may control fast gas valves 812 to provide "on/off" dose modulation and uniformity modulation respectively of the flow of reactive gas 814 to each element of plasma array 2. Alternatively, dose controller 801 and uniformity controller 802 may control power supply switches 816 to provide "on/off" dose modulation and uniformity modulation respectively of power supplies 818 powering plasma array 2. Also during a treatment procedure, dose controller 801 provides input to a scan system 820 which performs scanning of plasma array 2 across treatment area 500. During scanning, dose controller 801 computes the dose $\Delta D(x,y)$ delivered at each scan performed by scan system 820, and updates a computer dose matrix 822 accordingly. When dose matrix 822 corresponds to contour dose map 806, dose controller 801 instructs scan system 820 to stop scanning, and the treatment is complete.

Figure 9:
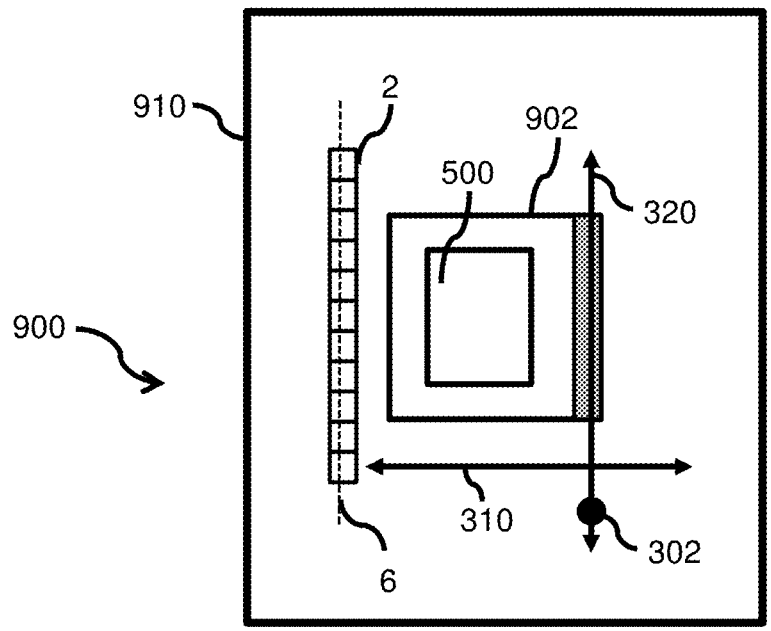
FIG. 9 is a diagram of a system incorporating an empirical calibration capability as an integral component.
Figure 9:
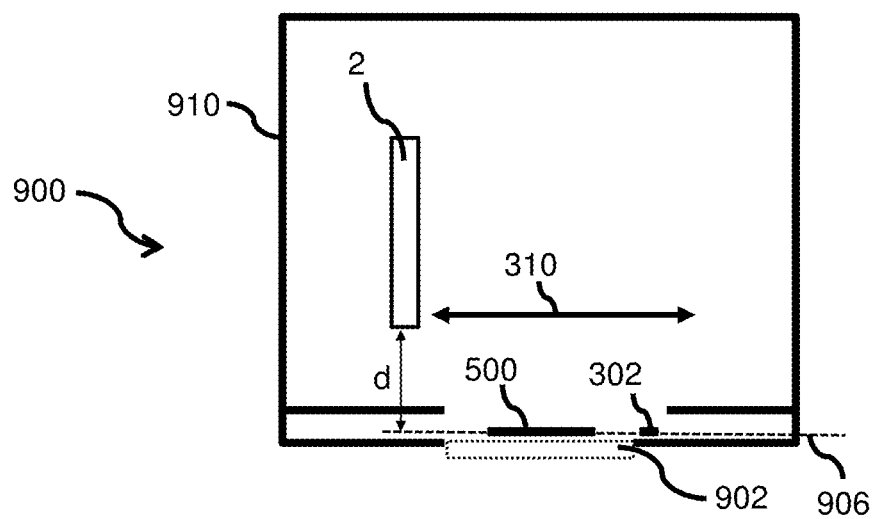

FIG. 9 shows a side view and top view of a treatment system 900 incorporating an empirical calibration capability as an integral component. System 900 is configured to perform an empirical calibration in-situ while plasma array 2 is being scanned to deliver a treatment of reactive species within treatment area 500. Treatment system 900 comprises a system enclosure 910 having a window opening 902 to expose treatment area 500. Treatment area 500 is co-planar in a treatment plane 906 with movable point probe 302. Movable point probe 302 may translated in motion direction 320, parallel to array axis 6, while plasma array 2 is scanned in scan direction 310 which is orthogonal to array axis 6.

Note that plasma array 2 can scan across both treatment area 500 and point probe 302, allowing point probe 302 to integrate reactive species output from plasma array 2 at a fixed location parallel to array axis 6. The integration may occur over one or more scans of plasma array 2. Point probe 302 may then move to a new location parallel to array axis 6, and repeat the integration. Thus, a reactive species output distribution such as that shown in graph 530 of FIG. 5A may be acquired in-situ during the treatment operation. A check of uniformity such as in step 224 of FIG. 2C may be performed in-situ, and empirical element scaling factors may be calculated and applied such as in steps 226 and 228 of FIG. 2C.

Point probe 302 may be a QCM sensor making in situ measurements of the reactive species by directly measuring change of mass of surface coating 304 on the QCM sensor. Alternatively, point probe 302 may directly measure species which are the result of interaction between a surface of treatment area 500 and the reactive species from plasma array 2. For example, point probe 302 may sense $C_xO_y$ type compounds formed by interaction between carbon in a biological surface and reactive oxygen in the plasma output.

What is claimed is:

1. A method of delivering a predetermined dose distribution of reactive species from a plasma to a treatment area with a predetermined treatment boundary, the method comprising the steps of:

providing a plasma array, the plasma array comprising a linear array of at least two plasma elements stacked linearly along an array axis, wherein each plasma element is an atmospheric plasma source and wherein each plasma element has an on state producing a reactive species output and an off state wherein the reactive species output is zero;

performing a calibration measurement, wherein the calibration measurement comprises:

activating the plasma elements to produce the reactive species output;

measuring a reactive species concentration for each one of the plasma elements; and, deriving an element scaling factor for each one of the plasma elements, wherein each element scaling factor is inversely proportional to the corresponding reactive species concentration;

scanning the plasma array across the treatment area with one or more scans in a back-and-forth scan direction perpendicular to the array axis; and, controlling each plasma element during the scanning with a uniformity modulation and a dose modulation, wherein the uniformity modulation controls the reactive species concentration of each plasma element to be proportional to the corresponding element scaling factor, and wherein the dose modulation controls the on state and the off state of each plasma element to deliver the predetermined dose distribution.

2. The method of claim 1 wherein the uniformity modulation comprises adjusting a power supply of each plasma element.

3. The method of claim 1 wherein the uniformity modulation comprises controlling each plasma element to have the on state for a percent on time, and the off state for a percent off time, wherein the percent on time of each plasma element is proportional to the corresponding element scaling factor.

4. The method of claim 1 wherein the dose modulation comprises the steps of:
maintaining each plasma element in the off state when the corresponding reactive species output is not coupled to the treatment area within the treatment boundary; and,
implementing the uniformity modulation of each plasma element when the corresponding reactive species output is coupled to the treatment area within the treatment boundary.

5. The method of claim 1 wherein the on state and the off state of each plasma element are controlled by operating a power supply switch for each plasma element, wherein each power supply switch controls delivery of a plasma power to the corresponding plasma element, and wherein the on state corresponds to closing the power supply switch to deliver the plasma power, and the off state corresponds to opening the power supply switch to cut off supply of the plasma power.

6. The method of claim 1 wherein the on state and the off state of each plasma element are controlled by operating a fast gas valve for each plasma element, wherein each fast gas valve controls flow of a reactive gas to the corresponding plasma element, and wherein the on state corresponds to opening the fast gas valve to deliver the reactive gas, and the off state corresponds to closing the fast gas valve to cut off supply of the reactive gas.

7. The method of claim 1 wherein the step of measuring the reactive species concentration further comprises the step of providing a detection system configured to produce a detector signal for each plasma element proportional to the corresponding reactive species concentration.

8. The method of claim 7 wherein each element scaling factor is inversely proportional to the corresponding detector signal.

9. The method of claim 7 wherein the detection system comprises a Fourier Transform Infrared (FTIR) detection system.

10. The method of claim 7 wherein the detection system comprises an Optical Emission Spectroscopy (OES) detection system.

11. The method of claim 1 wherein the calibration measurement further comprises an empirical calibration, the empirical calibration comprising the steps of:
providing a test surface comprising a material which is reactive with the reactive species;
applying the reactive species output to the test surface; and,
measuring a reaction rate with the test surface of the reactive species output of each plasma element;
wherein each element scaling factor is inversely proportional to the corresponding reaction rate.

12. The method of claim 11 wherein the test surface is a thin film, and measuring the reaction rate comprises measuring an etch rate of the thin film.

13. The method of claim 12 wherein the thin film is carbon.

14. The method of claim 12 wherein the thin film is deposited on a quartz crystal microbalance (QCM) sensor.

15. The method of claim 1 further comprising the steps of:
creating a two-dimensional dose matrix in a computer memory, wherein the dose matrix represents a delivered dose distribution of reactive species to the treatment area;
updating the dose matrix after each scan with a calculated incremental dose delivered at each location within the treatment area; and,
terminating the scanning when the delivered dose distribution corresponds to the predetermined dose distribution.

16. The method of claim 15 wherein the calculated incremental dose is given by $\Delta D(x,y)$, wherein $\Delta D(x,y)=R(x)/V(y)$, wherein x is a direction parallel to the array axis, y is a direction parallel to the scan direction, R is the reaction rate, and V is a scan velocity.

17. The method of claim 16 wherein at least one position sensor is provided to measure the scan velocity and a location of the plasma array relative to the treatment surface.

18. The method of claim 1 wherein the predetermined dose distribution is a constant dose within the treatment area.

19. The method of claim 1 wherein the atmospheric plasma source is a cold atmospheric plasma (CAP) source.

20. The method of claim 19 wherein the CAP source is a dielectric barrier discharge (DBD) plasma source.

21. The method of claim 19 wherein the CAP source is a radio frequency (RF) plasma source.

22. The method of claim 19 wherein the CAP source is a microwave plasma source.

23. The method of claim 1 wherein the treatment area is a biological surface.

* * * * *